(12) United States Patent
Albert et al.

(10) Patent No.: US 8,288,569 B2
(45) Date of Patent: Oct. 16, 2012

(54) CARBONYL ASYMMETRIC ALKYLATION

(75) Inventors: Martin Albert, Bruck am Ziller (AT); Hubert Sturm, Innsbruck (AT); Andreas Berger, Ebbs (AT); Peter Kremminger, Kufstein (AT)

(73) Assignee: Sandoz AG, Basel (CH)

( * ) Notice: Subject to any disclaimer, the term of this patent is extended or adjusted under 35 U.S.C. 154(b) by 451 days.

(21) Appl. No.: 12/223,096

(22) PCT Filed: Jan. 22, 2007

(86) PCT No.: PCT/EP2007/000516
§ 371 (c)(1),
(2), (4) Date: Sep. 22, 2010

(87) PCT Pub. No.: WO2007/082771
PCT Pub. Date: Jul. 26, 2007

(65) Prior Publication Data
US 2011/0009648 A1    Jan. 13, 2011

(30) Foreign Application Priority Data

Jan. 23, 2006  (GB) .................................. 0601286.8

(51) Int. Cl.
*C07D 307/87*   (2006.01)
*C07F 5/02*     (2006.01)
(52) U.S. Cl. ........................................... 549/469; 568/6
(58) Field of Classification Search ................. 549/469; 568/6
See application file for complete search history.

(56) References Cited

U.S. PATENT DOCUMENTS

| 4,650,884 A | 3/1987 | Bogeso |
| 4,943,590 A | 7/1990 | Boegesoe |

FOREIGN PATENT DOCUMENTS

| DE | 2657013 C2 | 11/1985 |
| EP | 0171943 | 2/1986 |
| EP | 0347066 | 12/1989 |
| EP | 1281707 | 2/2003 |
| EP | 1281707 A1 | 2/2003 |
| JP | 2005247710 | 9/2005 |
| WO | 9819511 | 5/1998 |
| WO | 00/12044 | 3/2000 |
| WO | 0012044 | 3/2000 |
| WO | 01/43525 | 6/2001 |
| WO | 01/51478 | 7/2001 |
| WO | 01/68631 | 9/2001 |
| WO | 03/006449 | 1/2003 |
| WO | 03/011278 | 2/2003 |
| WO | 2004/014821 | 2/2004 |
| WO | 2005066185 A1 | 7/2005 |

OTHER PUBLICATIONS

Ramon, D. J.; Yus, M. Angew. Chem. Int. Ed. 2004, 43, 284-287.
Broutin & Colobert, Eur. J. Org. Chem (2005), 1113-1128.
Hoffman et al., Chem. Ber. 122 (1989), 1783-1789.

*Primary Examiner* — Taofiq A Solola
(74) *Attorney, Agent, or Firm* — Jeffrey S. Melcher; Manelli Selter PLLC

(57) ABSTRACT

This invention relates to processes and intermediates for the stereoselective alkylation of carbonyl groups. The invention in particular allows the stereoselective preparation of the antidepressant drug escitalopram. It has been found that boric or boronic acid derivatives are useful bridging elements for the attachment of a chiral group to a compound containing a carbonyl group to be alkylated. The said borates and boronates are thus useful in a process for the asymmetric alkylation of a carbonyl group in a compound containing a carbonyl group and an anchor group capable of reacting with a boric or boronic acid derivative. The asymmetric alkylation can be carried out by admixing the compound containing a carbonyl group to be alkylated and the anchor group capable of reacting with a boric or boronic acid derivative with a boric or boronic acid derivative, adding a chiral alcohol, and adding an organometallic compound. After the alkylation reaction, the borate and boronate can be easily removed by hydrolysis.

29 Claims, No Drawings

CARBONYL ASYMMETRIC ALKYLATION

This application is the National stage of International Application No. PCT/EP2007/000516, filed on Jan. 22, 2007, which claims benefit under 35 U.S.C §119(e) of Great Britain Patent Application No. 0601286.8 filed on Jan. 23, 2006, the contents of both are incorporated herein by reference in their entirety.

This application is the National stage of International Application No. PCT/EP2007/000516, filed on Jan. 22, 2007, which claims benefit under 35 U.S.C. 119(e) and 365 of Great Britain Patent Application No. 0601286.8 filed on Jan. 23, 2006, the contents of both are incorporated herein by reference in their entirety.

FIELD OF INVENTION

This invention relates to processes and intermediates for the stereoselective alkylation of carbonyl groups. The invention in particular allows the stereoselective preparation of the antidepressant drug escitalopram.

BACKGROUND OF THE INVENTION

Methods for the asymmetric construction of quaternary carbon atoms are rare. This particularly applies for the synthesis of tertiary alcohols, which still represents a challenge for a synthetic organic chemist. The most direct approach for the asymmetric preparation of tertiary alcohols consists in a stereoselective addition of an organometallic reagent to a ketone. However, reagent controlled and catalyzed methods are limited to a few examples (see: Ramon, D. J.; Yus, M. *Angew. Chem. Int. Ed.* 2004, 43, 284-287). Thus, there is a need for methods for the preparation of chiral tertiary alcohols.

A tertiary alcohol of particular interest is compound of formula (II), which is the key intermediate in the production of the drug escitalopram (I), which is a well-established antidepressant. It is a selective, centrally acting serotonin (5-hydroxytryptamine; 5-HT) reuptake inhibitor, accordingly having antidepressant activities.

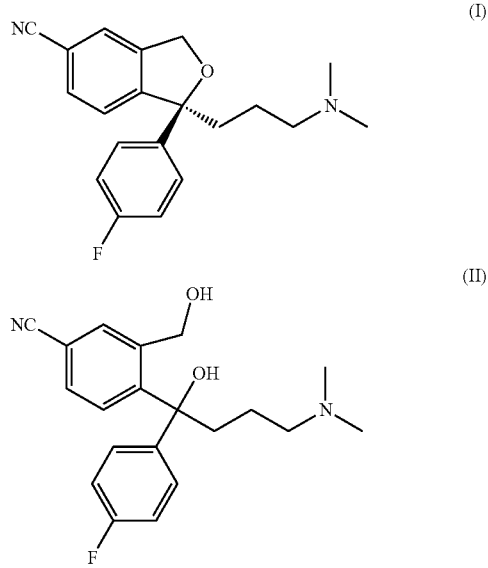

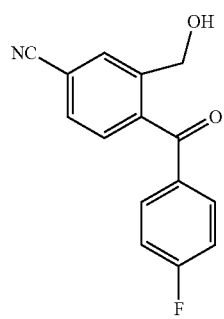

Escitalopram was first disclosed in EP 347066 by H. Lundbeck A/S. In this patent publication the substance is claimed and two methods for the preparation based on a separation of the R- and S-enantiomer of a synthesis intermediate are given followed by a conversion of enantiomerically pure diol (II) or labile esters thereof to escitalopram (I).

The first method includes a transformation of racemic 4-[4-dimethylamino-1-(4-fluoro-phenyl)-1-hydroxy-butyl]-3-hydroxymethyl-benzonitrile (formula (II)) into the corresponding two diastereomeric esters (by using a chiral acid chloride), which can be separated by chromatography on an achiral stationary phase or fractional crystallization. The ester with the desired stereochemistry is converted into escitalopram by a base promoted ring closure reaction. The racemic diol of formula (II) and its use in the synthesis of citalopram have been disclosed in U.S. Pat. No. 4,650,884.

The second method described in EP 347066 is based on a separation of the racemic diol of formula (II) by a classical resolution using (+)-di-O',O'-toluoyltartaric acid as resolving agent. The yield for this resolution according to EP 347066 is 55% (27.5% calculated on racemic diol (II)). The enantiomerically pure diol is submitted to a subsequent dehydrative ring closure reaction (MsCl, $Et_3N$) to give escitalopram.

In WO 03/006449 the separation of the enantiomers of diol (II) by preparative chromatography on a chiral stationary phase is disclosed. Ee's (enantiomeric excess) of more than 99% and yields of more than 95% (47.5% calculated on racemic diol (II)) can be obtained by this separation method. The large scale chromatography is technically realized by using SMB technology (SMB=simulated moving bed) on a carbohydrate based stationary phase. Conversion of enantiomerically pure diol (II) to escitalopram is performed according to EP 347066.

In WO04/014821 a fourth approach is disclosed, which relies on the use of enzymes (esterases and lipases) for the separation of the racemic diol of formula (II). A kinetic enzymatic acylation or deacylation of racemic diol (II) or esters of racemic diol (II), respectively, results in a mixture containing preferentially one of the enantiomers as diol of formula (II) and the second enantiomer as ester of diol (II). After separation the ring closure can be performed as described above.

All of the four described approaches to enantiopure escitalopram start from the racemic diol of formula (II). The theoretical overall yield of escitalopram obtained by any of these processes is limited to 50% based on racemic diol (II).

Though highly desirable an asymmetric synthesis to an enantiomerically enriched or pure diol of formula (II), which is not based on a separation of racemic diol (II), has not been reported so far. Such a synthesis would significantly increase the overall yield to escitalopram.

It has now been found that boric or boronic acid derivatives are useful bridging elements for the attachment of a chiral group to a compound containing a carbonyl group to be alkylated. The borates and boronates are thus useful in a process for the asymmetric alkylation of a carbonyl group in a compound containing a carbonyl group and a functional group (in the following referred to as "anchor" group) capable of reacting with a boric or boronic acid derivative. The asymmetric alkylation can be carried out by admixing the compound containing a carbonyl group to be alkylated and the anchor group capable of reacting with a boric or boronic acid derivative with a boric or boronic acid derivative, adding a chiral alcohol, and adding an organometallic compound. After the alkylation reaction, the borate and boronate can be easily removed by hydrolysis.

By using the process of the invention, the desired S-enantiomer of diol (II) (or the corresponding R-enantiomer) can be prepared in high yield. Thus, escitalopram can be synthesized without the need for separation of racemic diol (II).

THE INVENTION

The present invention relates to a process for the asymmetric alkylation of a carbonyl group in a compound (compound K) containing a carbonyl group and an anchor group capable of reacting with a boric or boronic acid derivative, comprising the steps of
a) admixing the compound K with a boric or boronic acid derivative;
b) adding a chiral auxiliary (compound A), and
c) adding an organometallic compound (R-M).

Scheme 1 exemplifies the process of the present invention by way of a preferred auxiliary, a chiral alcohol.

The process of the invention has the advantage that it is fast, economical, simple and produces chiral tertiary alcohols in high yield and in high enantiomeric excess. A further advantage is that the process of the invention can be carried out in a one-pot format.

bonyl group are within the same molecule. Preferred ways for how these two groups are linked are specified below.

Preferred boric or boronic acid derivatives are phenylboronic acid, trimethylborate, triisopropylborate, diisopropylbutylboronate, diisopropylmethylboronate, methylboronic acid or trimethylboroxine, in particular diisopropylmethylboronate, methylboronic acid or trimethylboroxine.

Preferred anchor groups (A-H) capable of reacting with a boric or boronic acid derivative are a hydroxyl group, an amino group, a carboxyl group and a sulfhydryl group, with a hydroxyl group being particularly preferred.

Preferred chiral auxiliaries (compound A) are chiral alcohols, in particular such chiral alcohols comprising the structural element of formula (VII)

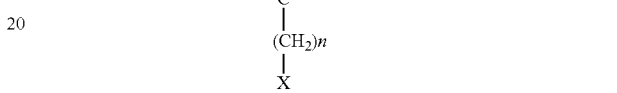

(VII)

wherein C* is a chiral carbon, wherein n is 1 and X is nitrogen, with the chiral amino alcohols N-methylephedrine, N-methylpseudoephedrine, 2-dimethylamino-1-phenylethanol, quinine, quinidine, cinchonidine, or cinchonine being particularly preferred.

Preferred organometallic compounds (R-M) for the stereoselective alkylation are organomagnesium compounds. In particular for the synthesis of the diol of formula (II), the preferred organomagnesium compound is N,N-dimethylaminopropyl magnesium chloride.

The diol of formula (II) can be further treated to undergo ring closure to form escitalopram.

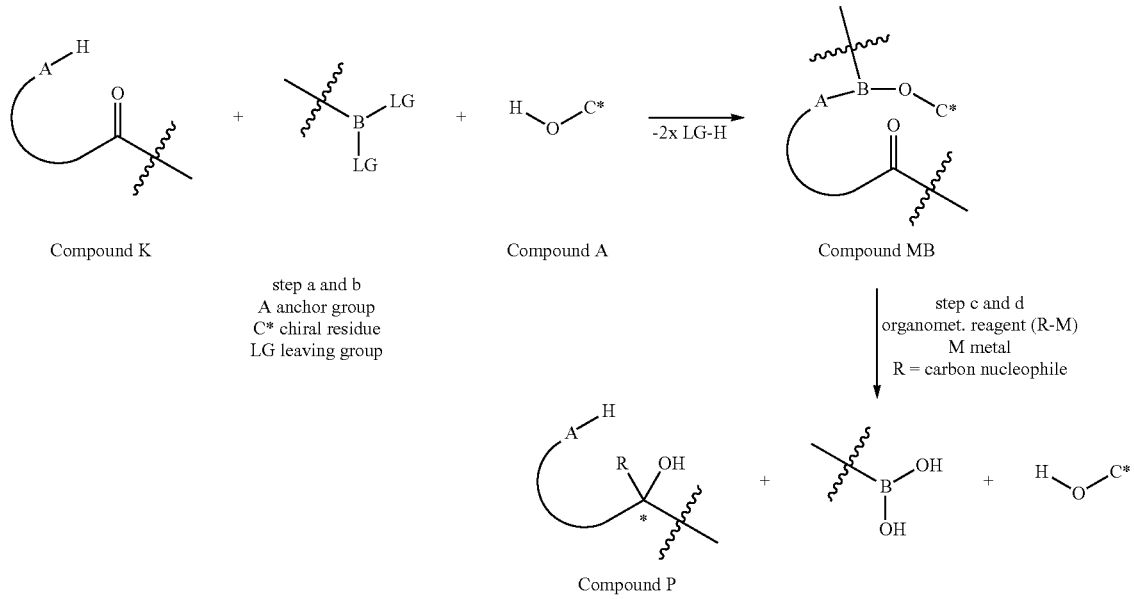

Scheme 1

Compound K      Compound A      Compound MB step a and b
A anchor group
C* chiral residue
LG leaving group step c and d
organomet. reagent (R-M)
M metal
R = carbon nucleophile Compound P The bonds marked with a toggled line indicate a bond to one of those residues as further defined below. The semicircle in compound K indicates that the anchor group and the car- The invention further relates to various intermediates formed during the new process, to the use of a borate or a boronate as a linker element between a starting compound containing a functional group suitable for nucleophilic substitution by a carbanion and an anchor group capable of reacting with a boric or boronic acid derivative and a chiral auxiliary capable of guiding a stereoselective reaction of a carbonyl group in the starting compound. The invention further relates to the hydroxyketone of formula (Ill) in crystalline form.

DETAILED DESCRIPTION OF THE INVENTION

The present invention relates to a process for the asymmetric alkylation of a carbonyl group, preferably a keto group, in a compound K, which compound K contains a carbonyl group and an anchor group capable of reacting with a boric or boronic acid derivative, comprising the steps of
a) admixing compound K with a boric or boronic acid derivative;
b) adding a chiral auxiliary group, like a chiral alcohol, and
c) adding an organometallic compound.

Scheme 1 exemplifies a preferred embodiment of the process of the present invention. Preferably, a final hydrolysis step d) is added after alkylation of the carbonyl group in step c) to yield a tertiary alcohol containing product (compound P).

Asymmetric alkylation means that one out of the two possible enantiomers of the product diol is preferentially formed. The addition of the metal organyl proceeds with stereofacial control in favor of one enantiomer of the product diol.

This implies that the addition of the organometallic compound (step c) to the chiral mixed boronate or borate (compound MB) obtained after steps a) and b) is diastereoselective.

The composition of the mixture obtained after addition of the organometallic compound to the mixed boronate or borate (compound MB) depends on the specific chiral auxiliary (compound A) used and the conditions under which the reaction is carried out.

Characteristic of the asymmetric addition according to the invention is that a considerably larger amount of one enantiomer of formula (II), the product (compound P), compared to the other is formed. The ratio of S- to R-enantiomer (or R to S) is different from 1 to 1, usually at least 10 to 1, preferably greater than 15 to 1.

The steps a), b), c), and—if present—also d), preferably take place in the same inert medium, preferably the medium is an aprotic solvent. Suitable organic solvents are toluene, tetrahydrofuran, acetonitrile, DMF, DMSO, dioxane, DME, diglyme, nitromethane, methyl tert-butyl ether, $CH_2Cl_2$, or NMP or mixtures thereof, with toluene and dimethoxyethane/tetrahydrofuran mixtures being particularly preferred.

Typically, the substrate compound K, the boric or boronic acid derivative and the chiral auxiliary (compound A), for example the chiral alcohol, are admixed in an aprotic solvent under mild conditions for a time sufficient to allow attachment of both the anchor group of the substrate and the chiral auxiliary, for example the chiral alcohol, to the boric or boronic acid derivative and thus generation of a substituted boric or boronic acid, wherein the boron atom links the chiral auxiliary compound to the substrate.

The order of steps a) and b) is not critical. The addition of substrate compound K, the chiral auxiliary compound, and the boric or boronic acid derivative to the reaction system can be carried out in arbitrary order.

Compound K may be first mixed with the boric or boronic acid derivative and then the chiral auxiliary, like the chiral alcohol, may be added, or compound K may be mixed with the chiral auxiliary, like the chiral alcohol, first and the boric or boronic acid derivative may then be added, or the chiral auxiliary, like the chiral alcohol, and the boric or boronic acid derivative may be added simultaneously to the substrate in the inert medium. In all cases, the substituted boric or boronic acid derivative, wherein the boron atom tethers the chiral auxiliary compound to the substrate, will form.

The condensation of the substrate compound K, the chiral auxiliary (compound A), and the boric or boronic acid derivative is performed with 0.8 to 1.8 equivalents of boric or boronic acid derivative relative to the substrate compound K, more preferably with 1.0 to 1.2 equivalents.

The condensation of the substrate compound K, the chiral auxiliary (compound A), and the boric or boronic acid derivative is performed with 0.8 to 2.0 equivalents of the chiral auxiliary relative to the substrate compound K, more preferably with 1.0 to 1.4 equivalents.

Depending on the particular boric or boronic acid derivative used in step a), water, an alcohol, an amine, or HX, wherein X=halogen, is formed during steps a) and b). These side products are preferably removed, for example by azeotropic distillation or by salt formation (in the case that the side product is HX) followed by filtration before addition of the organometallic compound of step c), in order to shift the equilibrium to the mixed boronate (compound MB). A skilled person will appreciate that in some cases active removal is not always necessary, for example if the side product generated is a gas insoluble in the solvent of the process steps. However, substantial removal of the side product from the reaction mixture is generally preferred. In a preferred embodiment, the side product is water or an alcohol and the reaction mixture is subjected to an azeotropic distillation before step c), wherein preferably the side products of steps a) and b) are substantially removed. If the side product is water, it is preferably removed to below 0.5% w/v and more preferably to below 0.1% w/v, as determined by Karl Fischer titration. If the side product is an alcohol, it is preferably removed to below 0.5% w/v and more preferably to below 0.1% w/v, as determined by gas chromatography.

Removal of water or alcohol can also be achieved by alternative methods known to the skilled person, for example removal by addition of molecular sieves or by reagents capable of withdrawing water, like e.g. drying agents.

If the side product is HX, removal by salt formation is preferred. This can be effected by addition of a suitable base, such as a tertiary amine.

The azeotropic distillation is preferentially carried out under reduced pressure. Such a distillation step typically takes up to 3 hours.

Preferred boric or boronic acid derivatives for the process of the present invention are those of formula VI,

(VI)

wherein $R_1$ is hydrogen, $C_{1-10}$-alkyl, $C_{2-10}$-alkenyl, $C_{2-10}$-alkynyl, $C_{6-10}$-aryl, $C_{7-16}$ alkaryl, a 4-10 membered heterocyclic residue, $C_{1-10}$-alkoxy, $C_{1-10}$-alkylamino, $C_{1-10}$-alkylthio, hydroxy, or cyano;
and wherein $R_2$ is halogen, hydroxy, $C_{1-10}$-alkoxy, $C_{6-10}$-aryloxy, $C_{1-10}$-dialkylamino, or a 4-10 membered heterocyclic residue connected by a S, N, or O atom to the boron atom;

and wherein R₃ is halogen, amino, hydroxy, C$_{1-10}$-alkoxy, C$_{6-10}$-aryloxy, C$_{1-10}$-dialkylamino, or a 4-10 membered heterocyclic residue connected by a S, N, or O atom to the boron atom;

or wherein R₂ and R₃ are connected to each other to form a 5-10 membered cyclic structure including the boron atom to which R₂ and R₃ are connected, wherein the cyclic structure may contain one or two additional boron, and/or oxygen, and/or nitrogen atoms.

It is more preferred that R₁ is C$_{1-10}$-alkyl, or C$_{1-10}$-alkoxy, in particular that R₁ is C$_{1-6}$-alkyl, with R₁ being methyl or ethyl, and in particular methyl, being most preferred.

In preferred borates and boronates R₂ and R₃ are identical and are hydroxy or C$_{1-10}$-alkoxy, for example methoxy, ethoxy, propoxy or isopropoxy. In a further preferred embodiment of the invention R₁ is methyl and R₂ and R₃ are hydroxy or C$_{1-10}$-alkyloxy. Alternatively R₁ is C$_{1-10}$-alkoxy and R₂ and R₃ are hydroxy or C$_{1-10}$-alkoxy. Thus, very preferred borates or boronates are phenylboronic acid, dimethoxymethyl borane, trimethylborate, triisopropylborate, diisopropylbutylboronate, diisopropylmethylboronate, methylboronic acid and trimethylboroxine, with diisopropylmethylboronate, methylboronic acid and trimethylboroxine being most preferred.

The use of these preferred borates and boronates has the advantage that water or alcohols are generated during steps a) and b) which can easily be removed from the reaction mixture before step c). This can, for example, be achieved by azeotropic distillation optionally under reduced pressure at ambient to mildly elevated (about 35 to 90° C.) temperatures or by addition of molecular sieves.

As far as the function of the anchor group is concerned, its purpose is to serve as an attachment site for the boric or boronic acid derivative. Preferred anchor groups for the process of the present invention are a hydroxyl group, a mono- or di-substituted substituted or unsubstituted amine, a carboxyl group or a sulfhydryl group, in particular a hydroxyl group.

Without being bound to any theory, it is believed that in preferred embodiments of the present invention the temporary boron tethered auxiliary group affects the stereochemistry of the transition state of the alkylation reaction. To facilitate the generation of a system suitable for stereochemical control of the alkylation reaction in step c), such substrates are preferred wherein the carbon atom of the carbonyl group to be alkylated is separated from the carbon atom carrying the anchor group by 1 to 6 Angstrom, preferably by 1.3 to 3 Angstrom. In order to fulfill this spatial requirement, the carbonyl group and the anchor group can be separated by numerous atoms in the substrate molecule, as long as there is an accessible configuration of the substrate molecule where the spatial requirement is fulfilled. Preferably, however, the carbon atom of the carbonyl group is separated from the carbon atom carrying the anchor group by 0 to 4 atoms, preferably by 1 to 4 carbon atoms, more preferably by 2 or 3 carbon atoms. For example, in the word BUT the letter B is separated from the letter T by one letter, the letter U.

Compound K is preferably selected from alpha-, beta-, gamma- and delta-hydroxy-ketones or aldehydes, alpha-, beta-, gamma- and delta-amino-ketones or aldehydes and alpha-, beta-, gamma- and delta-sulfhydryl-ketones or aldehydes, in particular gamma-hydroxy-ketones or aldehydes, gamma-amino-ketones or aldehydes and gamma-sulfhydryl-ketones or aldehydes. Ketones are preferred over aldehydes. Preferably, a phenyl substituent is placed adjacent to the keto group.

It is apparent to a person skilled in the art that other functional groups present in the substrate (compound K) which are not compatible with organometallic reagents or with the boric or boronic acid need to be protected.

The chiral auxiliary compound used in step b) of the process of the present invention may be a chiral amine or a chiral thiol, but is preferably a chiral alcohol, in particular comprising the structural element of formula (VII)

wherein C* is a chiral carbon, n is an integer from 0 to 3 and wherein X is a heteroatom having a free electron pair. Such heteroatoms are, for example oxygen, sulfur and nitrogen, with nitrogen being particularly preferred. It is preferred that n is 1 or that X is nitrogen, and it is most preferred that n is 1 and X is nitrogen. Without being bound to any theory, it is believed that in preferred embodiments of the present invention the heteroatom of the boron-attached auxiliary group is part of a system chelating the metal of the organometallic compound used in the alkylation step c), thus affecting the stereochemistry of the transition state of the alkylation reaction.

In those cases, where X is nitrogen, it is preferred that the nitrogen be part of a tertiary amine.

Preferred chiral amino alcohols are ephedrine derivatives, such as 1S,2S-N-methylpseudoephedrine, 1R,2R—N-methylpseudoephedrine, 1S,2R—N-methylephedrine, or 1R,2S-N-methylephedrine, or 1S-2-dimethylamino-1-phenyl ethanol or 1R-2-dimethylamino-1-phenyl ethanol, or cinchona alkaloids such as cinchonidine, quinidine, cinchonine, or quinine (for preferred chiral auxiliaries see also the scheme below; where only one enantiomer is shown, the skilled person will understand that the other enantiomer can be used to obtain a reciprocal result).

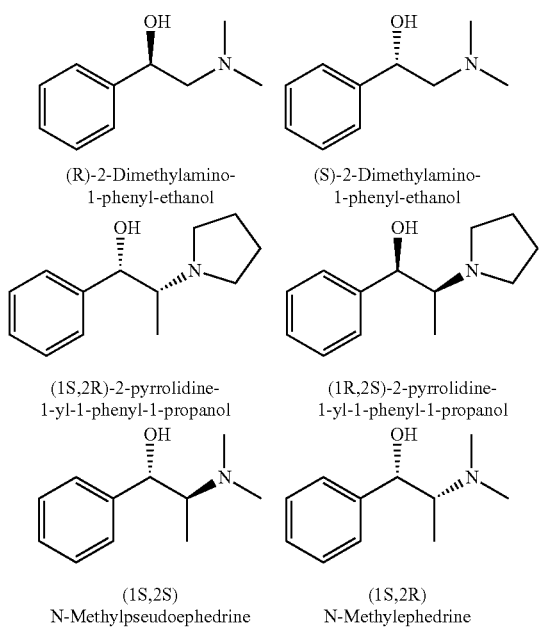

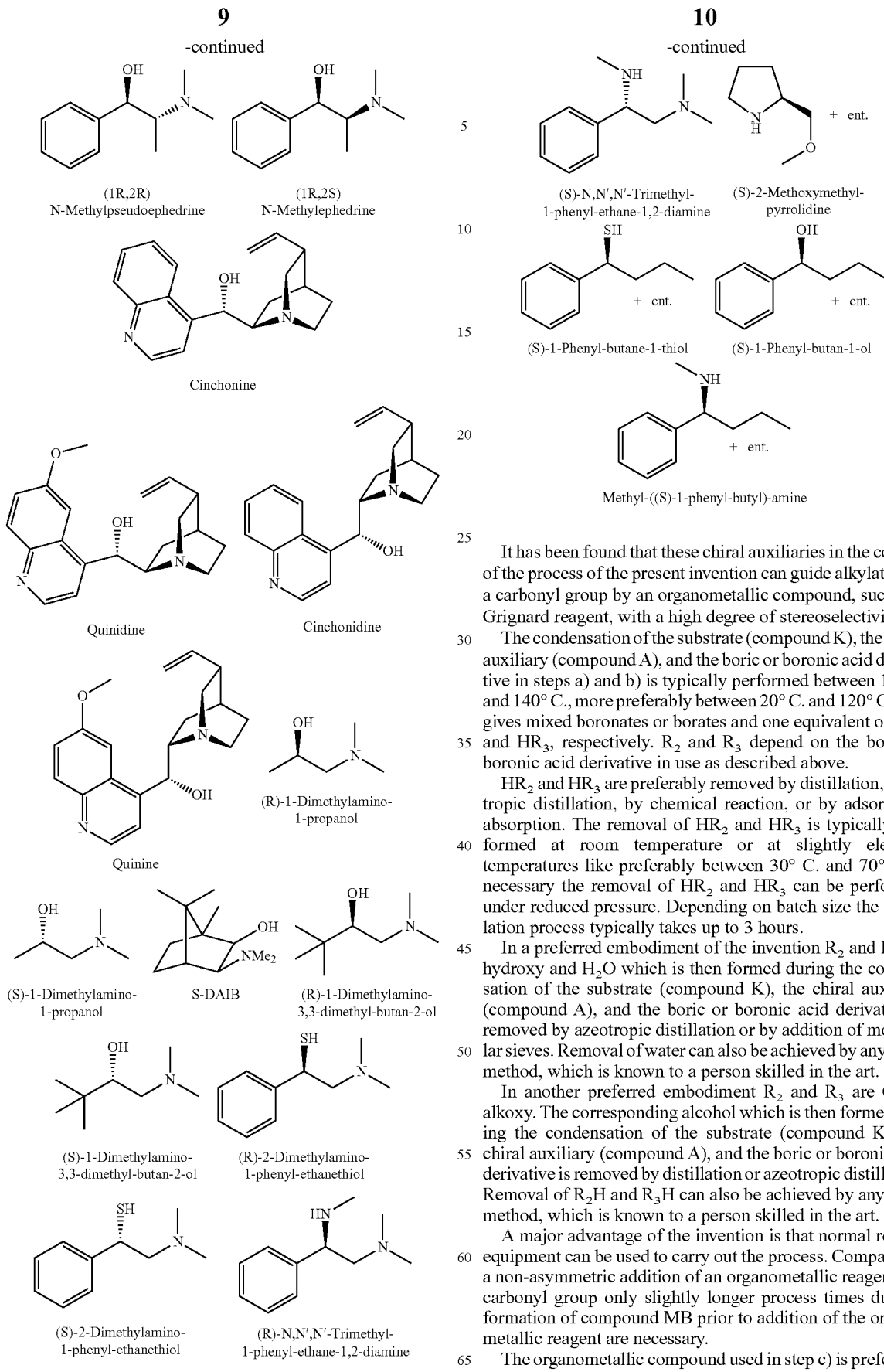

It has been found that these chiral auxiliaries in the context of the process of the present invention can guide alkylation of a carbonyl group by an organometallic compound, such as a Grignard reagent, with a high degree of stereoselectivity.

The condensation of the substrate (compound K), the chiral auxiliary (compound A), and the boric or boronic acid derivative in steps a) and b) is typically performed between 10° C. and 140° C., more preferably between 20° C. and 120° C., and gives mixed boronates or borates and one equivalent of $HR_2$ and $HR_3$, respectively. $R_2$ and $R_3$ depend on the boric or boronic acid derivative in use as described above.

$HR_2$ and $HR_3$ are preferably removed by distillation, azeotropic distillation, by chemical reaction, or by adsorption/absorption. The removal of $HR_2$ and $HR_3$ is typically performed at room temperature or at slightly elevated temperatures like preferably between 30° C. and 70° C. If necessary the removal of $HR_2$ and $HR_3$ can be performed under reduced pressure. Depending on batch size the distillation process typically takes up to 3 hours.

In a preferred embodiment of the invention $R_2$ and $R_3$ are hydroxy and $H_2O$ which is then formed during the condensation of the substrate (compound K), the chiral auxiliary (compound A), and the boric or boronic acid derivative is removed by azeotropic distillation or by addition of molecular sieves. Removal of water can also be achieved by any other method, which is known to a person skilled in the art.

In another preferred embodiment $R_2$ and $R_3$ are $C_{1-10}$-alkoxy. The corresponding alcohol which is then formed during the condensation of the substrate (compound K), the chiral auxiliary (compound A), and the boric or boronic acid derivative is removed by distillation or azeotropic distillation. Removal of $R_2H$ and $R_3H$ can also be achieved by any other method, which is known to a person skilled in the art.

A major advantage of the invention is that normal reactor equipment can be used to carry out the process. Compared to a non-asymmetric addition of an organometallic reagent to a carbonyl group only slightly longer process times due the formation of compound MB prior to addition of the organometallic reagent are necessary.

The organometallic compound used in step c) is preferably an organomagnesium, organozinc, organocadmium, organocerium, organolithium, organotitanium, organomanganese, organoaluminum, organoiron or organotin compound. Organometallic compounds, which are known to react under chelation control [and contain metals such as magnesium, titanium, cerium, iron, manganese, zinc, tin, aluminum] are preferred over non-chelating reagents which contain metals such as lithium or aluminum. It is preferred that the organometallic compound shows a relatively high degree of reactivity against a carbonyl group. For this reason, an organomagnesium compound, such as alkylmagnesium, alkenylmagnesium or alkinylmagnesium, is most preferred as the organometallic compound.

If the organometallic reagent is to transfer an alkyl or alkenyl residue to the carbonyl group, the alkylation step c) is typically performed between −100° C. and 20° C., more preferably between −60° C. and −30° C. At lower temperatures a better selectivity of the addition of the organometallic compound to the carbonyl group of the substrate compound K is observed. However, due to practical reasons reaction temperatures of −80° C. to −30° C. are preferred.

For a complete conversion 1 to 3 equivalents of the organometallic compound are used. Preferentially, 2 equivalents of the organometallic compound are added. The organometallic compound can be added in neat form or in solution.

In a preferred embodiment the organometallic compound is added in solution. The solvent can be any organic aprotic solvent. Suitable organic solvents are toluene, tetrahydrofuran, dioxane, dimethoxyethane, diglyme, methyl tert-butyl ether, or dimethoxymethane. Most preferentially, the solvent is tetrahydrofuran.

In a preferred embodiment Grignard reagents are used. By using such reagents the addition to the carbonyl group is fast and typically takes about 30 minutes depending upon the batch size.

Subsequent addition of water, aqueous salt solutions, aqueous acid, or aqueous base to the reaction after addition of the organometallic compound gives an enantiomerically enriched product compound P, the chiral auxiliary compound A, and boric or boronic acid.

Addition of water, aqueous acid, or aqeous base instantly leads to hydrolysis of the mixed borate or boronate. Instead of water, an excess of $C_{1-10}$ alcohols can be used. Thereby, the corresponding boric or boronic $C_{1-10}$ alkyl ester in addition to compound P and compound A is obtained.

The isolation of the product compound P out of the reaction mixture can be performed according to methods known to a person skilled in the art, wherein the isolation process depends on the chiral auxiliary compound in use. Such methods include extraction, distillation, crystallization, or chromatography.

The exact composition of the product mixture obtained after addition of the organometallic compound to the mixed boronate or borate obtained after steps a) and b) depends on the specific chiral auxiliary compound used and the conditions under which the reaction is carried out. Characteristic of the asymmetric addition according to the invention is that a considerably larger amount of one enantiomer of the product compound P compared to the other is formed. The product (compound P) is typically obtained with an enantiomeric excess (ee) of >50%. In a preferred embodiment the ee is greater than 90%.

The conversion of the substrate (compound K) to the product (compound P) is greater than 50%, usually greater than 95%, more preferably greater than 98%. Addition of more than 1 equivalent of organometallic reagent (step c) gives better conversions. Preferentially, 2 equivalents of the organometallic compound are added. The organometallic compound can be added in neat form or in solution.

The optical purity of the product diol obtained after isolation may be even further improved before further processing. Improvement of the optical purity may be achieved, e.g. by crystallization of diastereomeric esters or salts with optically active acids as described in U.S. Pat. No. 4,943,590 or by chromatography as described in WO03/011278 or by other methods.

The present invention relates, in a preferred embodiment, to a process for the preparation of a key intermediate for the synthesis of escitalopram, the diol of formula (II). Thus, in a preferred embodiment, the compound K used in step a) is a compound of formula (III)

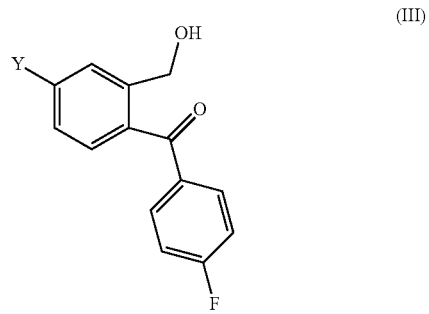

(III)

wherein Y is cyano or a group which is convertible to a cyano group, the organometallic compound used in step c) is an organometallic compound of formula (VIII)

(VIII)

wherein M is a metal, and
Z is —$CH_2$—$N(CH_3)_2$ or a group which may be converted to —$CH_2$—$N(CH_3)_2$, such as —$CH_2$-LG, —$CH_2$—$NO_2$, —CN, —C—$N_3$, —CHO, —$CH_2$—OPg, —$CH_2$—$NH_2$, —$CH_2$—$NHCH_3$, —$CH_2$—$NPg_1Pg_2$, —$CH_2$—$NPg_1CH_3$, —CO—$N(CH_3)_2$, —$CH(Q_1R_{11})(Q_2R_{12})$, —$C(Q_1R_{13})(Q_2R_{14})(Q_3R_{15})$, —$COOR_{16}$, —$CH_2$—CO—$NH_2$, —CH=CH—$R_{17}$, or —$CONHR_{18}$, wherein Pg is a protection group for an alcohol, $Pg_1$ and $Pg_2$ are protection groups for an amino group, $R_{11}$ and $R_{12}$ are independently selected from $C_{1-6}$ alkyl, $C_{2-6}$ alkenyl, $C_{2-6}$ alkynyl and optionally $C_{1-6}$ alkyl substituted aryl or aryl-$C_{1-6}$ alkyl or $R_{11}$ and $R_{12}$ together form a chain of 2 to 4 carbon atoms, each of $R_{13}$ to $R_{17}$ are independently selected from $C_{1-6}$ alkyl, $C_{2-6}$ alkenyl, $C_{2-6}$ alkynyl and optionally $C_{1-6}$ alkyl substituted aryl or aryl-$C_{1-6}$ alkyl, R18 is hydrogen or methyl and Q1, Q2, and Q3 are selected from O and S; L is a leaving group such halogen or —O—$SO_2$—$R_{11}$ and $R_{11}$ defined as above. Such transformations (Z to —$CH_2$—$N(CH_3)_2$) are described in WO01/43525, WO01/51478, WO01/68631, and WO04/014821.

The dotted line of organometallic compound of formula (VIII) can be a single, double, or triple bond, and M is any metal or metal derivative, and preferably is Mg, and wherein Z is —$CH_2$—$N(CH_3)_2$ or a group that may be converted to —$CH_2$—$N(CH_3)_2$. Preferably, the dotted line is a single bond and M is magnesium or magnesium chloride and Z is —$CH_2$—$N(CH_3)_2$.

In another preferred embodiment the dotted line of the organometallic reagent of formula (VIII) is a triple bond and M is magnesium or magnesium chloride or bromide.

If the dotted line is a double or a triple bond, the conversion of the mixed boronate V to the product diol (II) is performed between −40° C. and 40° C., more preferably between 0° C. and 30° C. The resulting compound can be converted to diol of formula (II) by reduction.

A diol of formula (II) is obtained in enantiomerically enriched or enantiomerically pure form

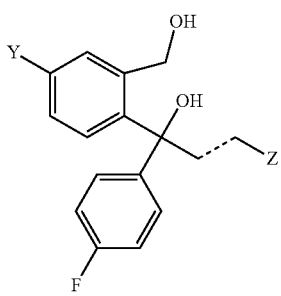

(II)

wherein Y is cyano or a group which is convertible to a cyano group, by this particularly preferred process of the invention. The diol of formula (II) can then be used for escitalopram synthesis. Thus, the present invention further relates to a process comprising the further step of ring closure of the diol of formula (II) to form a compound of formula (IX), wherein Y and Z are as defined herein.

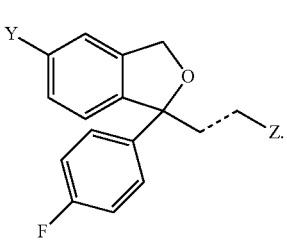

(IX)

The preferred compound of formula (IX) is escitalopram.

The conversion of diol of formula (II) to escitalopram can be performed as described in U.S. Pat. No. 4,943,590. More preferably, ring closure of compound of formula (II) may be carried out by treatment of a carbonic, carboxylic, sulfinic or sulfonic ester derivative of the compound with a base such as $KOC(CH_3)_3$ and other alkoxides, NaH or other hydrides, tertiary amines such as triethylamine, ethyldiisopropylamine or pyridine, at lower temperatures in an inert organic solvent such as tetrahydrofuran, toluene, DMSO, DMF, t-butyl methyl ether, dimethoxyethane, dimethoxymethane, dioxane, acetonitrile, or $CH_2Cl_2$.

If Z is not —$CH_2$—$N(CH_3)_2$, the transformation of the Z group to —$CH_2$—$N(CH_3)_2$ can be carried out before or after ring closure and is performed according to methods known to a person skilled in the art.

If Y is not a cyano group, the transformation of Y to a cyano group can be carried out before or after ring closure and is performed according to methods known to a person skilled in the art.

If the dotted line is a double or triple bond, the hydrogenation can be performed before or after ring closure according to methods known to a person skilled in the art.

The present invention further relates to intermediates of the process of the present invention, for example to a compound of formula (V), which is a useful intermediate for the synthesis of escitalopram,

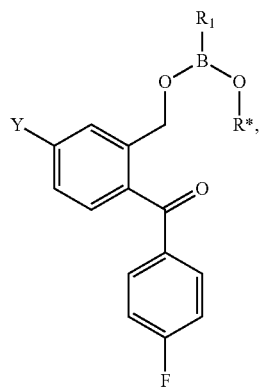

(V)

wherein $R_1$ is $R_1$ is $C_{1-10}$-alkyl or $C_{1-10}$-alkoxy, more preferably wherein $R_1$ is —$CH_3$, —$OCH_3$, or —$OCH(CH_3)_2$; wherein Y is cyano or a group which is convertible to a cyano group; and wherein O—R* is the residue of a chiral alcohol. The group which is convertible to a cyano group can be chloro, bromo, iodo, or $CF_3$—$(CF_2)_n$—$SO_2$—O—, wherein n is 0-8, $CH_2OH$ or protected $CH_2OH$, $CH_2NH_2$ or a protected $CH_2NH_2$, —$CH_2Cl$, —$CH_2Br$, —$CH_3$, —$NHR_2$, —$OR_2$, wherein $R_2$ is hydrogen or $C_{1-6}$ alkylcarbonyl; $CONR_3R_4$ wherein $R_3$ and $R_4$ are selected from hydrogen, optionally substituted $C_{1-6}$ alkyl, aryl-$C_{1-6}$ alkyl or aryl, or $R_3$ and $R_4$ are linked together to form a 5- or 6-membered ring optionally comprising a S, O, or additional N atom; or $CHOR_5OR_6$ wherein $R_5$ and $R_6$ are independently selected from alkyl, aryl, heteroaryl, or $R_5$ and $R_6$ are linked together to form a 5- or 6-membered ring; or other protected —CHO groups. Optionally Y may be a substituted oxazole, 4,5-dihydrooxazole, thiazole, or 4,5-dihydrothiazole group.

Mixed borate or boronate of formula (V) can be isolated or transformed to a diol of formula (II) in one pot reaction without isolation.

The isolation of a compound of formula (V) can be performed according to methods known to a person skilled in the art. In a preferred embodiment boronate or borate of formula (V) is isolated by removal of the solvent under reduced pressure and crystallization of the compound by addition of another solvent. Such a crystallization solvent can be, e.g. diethylether or tert-butyl methyl ether. However, the invention is not limited to these two solvents. Depending on the amino alcohol and boric or boronic acid used for the formation of compound (V) the isolation process can vary.

Mixed boronate (V) can be isolated or transformed in situ to diol of formula (II). In a preferred embodiment of the invention mixed boronate/borate of formula (V) is directly converted to diol (II).

In a further embodiment, the present invention relates to the hydroxyketone of formula (III) in crystalline form.

Hydroxyketone (III) can be prepared from 5-substituted phthalide derivatives, wherein Y is cyano or a group which may be converted to a cyano group.

Groups which may be converted to a cyano group include halogen such as chloro, bromo, or iodo, preferably chloro or bromo. Other groups which may be converted to cyano include $CF_3$—$(CF_2)_n$—$SO_2$—O—, wherein n is 0-8, —OH, —CHO, —$CH_2OH$, —$CH_2NH_2$, —$CH_2NO_2$, —$CH_2Cl$, —$CH_2Br$, —$CH_3$, —$NHR_8$, —CHNOH, —$COOR_9$, —$CONR_9R_{10}$ wherein $R_8$ is hydrogen or $C_{1-6}$ alkylcarbonyl, and $R_9$ and $R_{10}$ are selected from hydrogen, optionally substituted $C_{1-6}$ alkyl, aryl-$C_{1-6}$ alkyl and aryl.

Groups which may be converted to a cyano group also include optionally substituted oxazole, 4,5-dihydrooxazole, thiazole, or 4,5-dihydrothiazole groups.

Hydroxyketone (III) can, for example, be prepared from 5-cyanophthalide by addition of a 4-fluorophenyl magnesium halide, as described in EP0171943. The halide can be chloride, bromide, or iodide. The reaction can be performed in an ether solvent, in a mixture of ether solvents, in aliphatic or aromatic solvents, or mixtures thereof.

According to one embodiment of the invention hydroxyketone (III) is isolated by crystallization after aqueous work up. The solvent used for the crystallization can be an ether solvent, an aliphatic or aromatic solvent, an alcohol, water, or mixtures thereof.

In a preferred embodiment Y is a cyano group and hydroxyketone (III) is crystallized from diisopropylether, toluene, or ethylbenzene. Most preferably compound (III) is crystallized from toluene.

EXAMPLES

The following examples describe the present invention in detail, but they are not to be construed to be in any way limiting for the present invention.

Example 1

1S,2S-N-Methylpseudoephedrine as amino alcohol, −80° C. in toluene, diisopropoxymethyl borane as linker, isolation of 4-[(S)-(4-dimethylamino)-1-(4-fluorophenyl)-1-hydroxybutyl]-3-hydroxymethyl-benzonitrile, hemi (+)-di-O-toluoyl-tartaric acid salt 1.44 g of 4-(4-fluorobenzoyl)-3-hydroxymethyl-benzonitrile (5.6 mmol, 1.0 eq.) and 1.01 g of 1S,2S-N-methylpseudoephedrine (5.6 mmol, 1.0 eq.) are dissolved in a two-necked round bottomed flask in 20 mL of toluene under an inert atmosphere ($N_2$). At room temperature 1.17 mL of diisopropoxymethyl borane 97% (6.3 mmol, 1.13 eq.) are added. After 2 minutes a clear solution is obtained. The reaction mixture is warmed to 70° C. for 30 minutes. The reaction mixture is then cooled to 45° C. and ~18 mL of a mixture of toluene/2-propanol is gently removed under reduced pressure (~60 mbar) within 30 minutes. 20 mL of toluene are added and the reaction mixture is cooled to −80° C. 4.16 mL (2 eq.) of a 2.7M solution of dimethylaminopropyl magnesium chloride in THF is slowly added (duration: 5 minutes). Stirring is continued for 10 minutes at −80° C. HPLC control indicated a conversion of >98%. The ratio of S-diol (4-[(S)-4-dimethylamino-1-(4-fluorophenyl)-1-hydroxy-butyl]-3-hydroxymethyl-benzonitrile) to R-diol (4-[(R)-4-dimethylamino-1-(4-fluorophenyl)-1-hydroxy-butyl]-3-hydroxymethyl-benzonitrile) is 95.0:5.0 (enantiomeric excess=90.0%).

The reaction mixture is slowly added to 12 mL of cold 2M aqueous $H_2SO_4$. The layers are separated and the toluene layer is washed once with 3 mL of cold 2M aqueous $H_2SO_4$. The toluene layer is discarded. The aqueous layers are combined and 15 mL of MTBE is added. The pH is adjusted to 9 with 5M aqueous NaOH. After phase separation the aqueous layer is extracted once again with 10 mL of MTBE at pH 9. The MTBE is removed under reduced pressure. The crude product is purified by column chromatography (eluent ethyl acetate/cyclohexane/$Et_3N$ 1/1/0.1) on silica gel. The product containing fractions are combined and the solvent is removed under reduced pressure. Crystallization in 12 mL of 2-propanol with 1.05 g of (+)-di-O-toluoyl tartaric acid gives 2.3 g of (S)-4-(4-dimethylamino)-1-(4-flourophenyl)-1-hydroxy-butyl-3-hydroxymethylbenzonitrile, hemi (+)-di-O-toluoyl-tartaric acid salt (contains 0.5 equivalents of 2-propanol and water) in 71% yield (ee=99%, mp 134° C.).

$^1$H-NMR (DMSO-$d_6$, 300 MHz) 0.1.04 (d, 2×$CH_{3\ ISO}$, 6/2H, J 6 Hz), 1.26 (m, $CH_{2\ DIOL}$, 1H), 1.53 (m, $CH_{2\ DIOL}$, 1H), 2.13 (m, $CH_{2\ DIOL}$, 1H), 2.27 (m, $CH_{2\ DIOL}$, 1H), 2.37 (bs, 2×$CH_{3\ DTTA}$+N($CH_3$)$_{2\ DIOL}$, 9H) 2.71 (m, $CH_{2\ DIOL}$, 2H), 3.78 (m, $CH_{ISO}$, 1/2H), 4.02 (d, $CH_2OH_{DIOL}$, 1H, J 15.7 Hz), 4.57 (d, $CH_2OH_{DIOL}$, 1H, J 15.7 Hz), 5.70 (s, $CHOR_{DTTA}$, 2/2H), 7.07 (t, 2H, J 8.7 Hz), 7.21 (m, 2H), 7.33 (d, 2H, J 9 Hz), 7.74-7.91 (m, 5H).

Example 2

1S,2S-N-Methylpseudoephedrine as amino alcohol, −60° C. in toluene, diisopropoxymethyl borane as linker 143 mg of 4-(4-fluorobenzoyl)-3-hydroxymethyl-benzonitrile (0.56 mmol, 1.0 eq.) and 101 mg of 1S,2S-N-methylpseudoephedrine (0.56 mmol, 1.0 eq.) are dissolved in a two-necked round bottomed flask in 5 mL of toluene under an inert atmosphere ($N_2$). At room temperature, 118 µL of diisopropoxymethyl borane 97% (0.63 mmol, 1.14 eq.) is added. The clear solution is warmed to 70° C. for 30 minutes. The reaction mixture is then cooled to 45° C. and ~4.5 mL of a mixture of toluene/2-propanol is gently removed under reduced pressure (~60 mbar) within 30 minutes. 20 mL of toluene is added and the reaction mixture is cooled to −60° C. 420 µL (2 eq.) of a 2.7M solution of dimethylaminopropyl magnesium chloride in THF is slowly added (duration: 5 minutes). Stirring is continued for 10 minutes at −60° C. HPLC control indicated a conversion of >98%. The ratio of S-diol (4-[(S)-4-dimethylamino-1-(4-fluorophenyl)-1-hydroxy-butyl]-3-hydroxymethyl-benzonitrile) to R-diol (4-[(R)-4-dimethylamino-1-(4-fluorophenyl)-1-hydroxy-butyl]-3-hydroxymethyl-benzonitrile) is 91.0:9.0 (enantiomeric excess=82.0%).

Example 3

1S,2S-N-Methylpseudoephedrine as amino alcohol, −60° C. in THF, diisopropoxymethyl borane as linker 278 mg of 4-(4-fluorobenzoyl)-3-hydroxymethyl-benzonitrile (1.09 mmol, 1.0 eq.) and 250 mg of 1S,2S-N-methylpseudoephedrine (1.39 mmol, 1.3 eq.) are dissolved in a two-necked round bottomed flask in 5 mL of toluene under an inert atmosphere ($N_2$). At room temperature, 286 µL of diisopropoxymethyl borane 97% (1.55 mmol, 1.4 eq.) is added. The clear solution is warmed to 70° C. for 30 minutes. The reaction mixture is then cooled to 45° C. and ~4.5 mL of a mixture of toluene/2-propanol is gently removed under reduced pressure (~60 mbar) within 30 minutes. 5 mL of tetrahydrofuran is added and the reaction mixture is cooled to −60° C. 840 µL (2 eq.) of a 2.7M solution of dimethylaminopropyl magnesium chloride in THF is slowly added (duration: 5 minutes). Stirring is continued for 10 minutes at −60° C. HPLC control indicated a conversion of >98%. The ratio of S-diol (4-[(S)-4-dimethylamino-1-(4-fluorophenyl)-1-hydroxy-butyl]-3-hydroxymethyl-benzonitrile) to R-diol (4-[(R)-4-dimethylamino-1-(4-fluorophenyl)-1-hydroxy-butyl]-3-hydroxymethyl-benzonitrile) is 91.9:8.1 (enantiomeric excess=83.8%).

Example 4

1S,2S-N-Methylpseudoephedrine as amino alcohol, isolation of mixed boronate, methylboronic acid as linker 1.44 g of 4-(4-fluorobenzoyl)-3-hydroxymethyl-benzonitrile (5.64 mmol, 1.0 eq.) and 1.01 g of 1S,2S-N-methylpseudoephedrine (5.64 mmol, 1.1 eq.) are dissolved in a two-necked round bottomed flask in 20 mL of toluene under an inert atmosphere ($N_2$). At room temperature, 348 mg of methylboronic acid (5.81 mmol, 1.03 eq.) is added. The heterogeneous mixture is warmed to 70° C. Within 30 minutes the solution becomes homogeneous. The reaction mixture is then cooled to 45° C. and 12 mL of a mixture of toluene/$H_2O$ is gently removed under reduced pressure (~60 mbar) within 30 minutes. 12 mL of toluene is added and 12 mL of a mixture of toluene/$H_2O$ is gently removed under reduced pressure (~60 mbar) within 30 minutes. 20 mL of diethyl ether is added and the reaction is cooled to 0° C. After 30 minutes white crystals start to precipitate. Crystallization is complete after 15 hours. The crystals are separated by filtration under an inert atmosphere to give 2.3 g (91%) of mixed boronate.

$^1$H-NMR (CDCl$_3$) −0.2 (s, 3H), 0.99 (d, 3H, J 7.0 Hz), 2.31 (s, 6H), 3.1-3.3 (m, 1H), 4.44 (d, 1H, J 9.6 Hz), 4.64 (d, 1H, J 14.9 Hz), 4.71 (d, 1H, 14.9 Hz), 7.0-8.1 (m, 12H).

2.3 g of mixed boronate are dissolved in 20 mL of toluene. At −60° C. 2.8 mL (2.0 eq.) of a 3.6M solution of dimethylaminopropyl magnesium chloride in THF are slowly added (duration: 5 minutes). Stirring is continued for 10 minutes at −60° C. HPLC control indicated a conversion of >95%. The ratio of S-diol (4-[(S)-4-dimethylamino-1-(4-fluorophenyl)-1-hydroxy-butyl]-3-hydroxymethyl-benzonitrile) to R-diol (4-[(R)-4-dimethylamino-1-(4-fluorophenyl)-1-hydroxy-butyl]-3-hydroxymethyl-benzonitrile) is 89.1:10.9 (enantiomeric excess=78.2%).

Example 5

1S,2S-N-Methylpseudoephedrine as amino alcohol, −65° C. in toluene, diisopropoxymethyl borane as linker, isolation of 4-[(S)-(4-dimethylamino)-1-(4-fluorophenyl)-1-hydroxybutyl]-3-hydroxymethyl-benzonitrile, hemi (+)-di-O-toluoyl-tartaric acid salt 1.42 g of 4-(4-fluorobenzoyl)-3-hydroxymethyl-benzonitrile (5.6 mmol, 1.0 eq.) and 1.00 g of 1S,2S-N-methylpseudoephedrine (5.6 mmol, 1.0 eq.) are dissolved in a two-necked round bottomed flask in 20 mL of toluene under an inert atmosphere ($N_2$). At room temperature, 1.17 mL of diisopropoxymethyl borane 97% (6.3 mmol, 1.13 eq.) are added. After 2 minutes a clear solution is obtained. The reaction mixture is warmed to 50° C. for 30 minutes. The reaction mixture is then cooled to 45° C. and ~20 mL of a mixture of toluene/2-propanol is gently removed under reduced pressure (~70 mbar) within 20 minutes. 20 mL of toluene is added and the reaction mixture is cooled to −65° C. 3.36 mL (2 eq.) of a 3.25M solution of dimethylaminopropyl magnesium chloride in THF is slowly added (duration: 10 minutes). Stirring is continued for 10 minutes at −65° C. HPLC control indicated a conversion of >99%. The ratio of S-diol (4-[(S)-4-dimethylamino-1-(4-fluorophenyl)-1-hydroxy-butyl]-3-hydroxymethyl-benzonitrile) to R-diol (4-[(R)-4-dimethylamino-1-(4-fluorophenyl)-1-hydroxy-butyl]-3-hydroxymethyl-benzonitrile) is 95.2:4.8 (enantiomeric excess=90.4%).

The reaction mixture is slowly added to 12 mL of cold 2M aqueous $H_2SO_4$. The layers are separated and the toluene layer is washed once with 3 mL of cold 2M aqueous $H_2SO_4$. The toluene layer is discarded. The aqueous layers are combined and 15 mL of methyl tert-butyl ether are added. The pH is adjusted to 9 with 5M aqueous NaOH. After phase separation the aqueous layer is extracted with 10 mL of methyl tert-butyl ether at pH 9. The combined organic layers are washed twice with 0.2M aqueous pivalic acid. The combined pivalic acid layers are extracted twice with 10 mL of methyl tert-butyl ether. The combined methyl tert-butyl ether (~40 mL) layers are washed with 5 mL of 5M aqueous NaOH. After phase separation, the major part of methyl tert-butyl ether is removed under reduced pressure. 12 mL of 2-propanol are added. At 35° C. 1.04 g of (+)-di-O-toluoyl tartaric acid are added. Within 5 minutes crystals start to form. After 4 h the white precipitate is removed by filtration to give 2.2 g of the title compound (69% yield, ee=99%, mp 134° C.).

Example 6

1S,2R—N-Methylephedrine as amino alcohol, −80° C., methylboronic acid as linker 142 mg of 4-(4-fluorobenzoyl)-3-hydroxymethyl-benzonitrile (0.56 mmol, 1.0 eq.) and 100 mg of 1S,2R—N-methylephedrine (0.56 mmol, 1.0 eq.) are dissolved in a two-necked round bottomed flask in 2 mL of toluene under an inert atmosphere ($N_2$). At room temperature, 36.1 mg of methylboronic acid (0.60 mmol, 1.08 eq.) are added. The reaction mixture is brought to 70° C. and stirred at this temperature for 30 minutes. The solvent is gently removed under reduced pressure within 5 minutes. 2 mL of toluene is added and removed again under reduced pressure. 2 mL of toluene is added and the reaction mixture is cooled to −80° C. 410 µL (2 eq.) of a 2.7M solution of dimethylaminopropyl magnesium chloride in THF is slowly added (duration: 10 minutes). Stirring is continued for 10 minutes at −80° C. HPLC control indicated a conversion of >90%. The ratio of S-diol (4-[(S)-4-dimethylamino-1-(4-fluorophenyl)-1-hydroxy-butyl]-3-hydroxymethyl-benzonitrile) to R-diol (4-[(R)-4-dimethylamino-1-(4-fluorophenyl)-1-hydroxy-butyl]-3-hydroxymethyl-benzonitrile) is 88.0:12.0 (enantiomeric excess=76.0%).

Example 7

1S,2R—N-Methylephedrine as amino alcohol, −80° C., trimethylboroxine as linker 142 mg of 4-(4-fluorobenzoyl)-3-hydroxymethyl-benzonitrile (0.56 mmol, 1.0 eq.) and 100 mg of 1S,2R—N-methylephedrine (0.56 mmol, 1.0 eq.) are dissolved in a two-necked round bottomed flask in 2 mL of toluene under an inert atmosphere ($N_2$). At room temperature 26 µL of trimethylboroxine (0.60 mmol, 0.3 eq.) are added. The reaction mixture is brought to 70° C. and stirred at this temperature for 30 minutes. The solvent is gently removed under reduced pressure within 5 minutes. 2 mL of toluene is added and removed again under reduced pressure. 2 mL of toluene is added and the reaction mixture is cooled to −80° C. 410 µL (2 eq.) of a 2.7M solution of dimethylaminopropyl magnesium chloride in THF is slowly added (duration: 10 minutes). Stirring is continued for 10 minutes at −80° C. HPLC control indicated a conversion of >98%. The ratio of S-diol (4-[(S)-4-dimethylamino-1-(4-fluorophenyl)-1-hydroxy-butyl]-3-hydroxymethyl-benzonitrile) to R-diol (4-[(R)-4-dimethylamino-1-(4- fluorophenyl)-1-hydroxy-butyl]-3-hydroxymethyl-benzonitrile) is 84.2:15.8 (enantiomeric excess=68.4%).

Example 8

(−)-Cinchonidine as amino alcohol, −80° C., diisopropoxymethyl borane as linker 83 mg of 4-(4-fluorobenzoyl)-3-hydroxymethyl-benzonitrile (0.28 mmol, 1.0 eq.) and 100 mg of (−)-cinchonidine 96% (0.32 mmol, 1.16 eq.) are dissolved in a two-necked round bottomed flask in 2 mL of toluene under an inert atmosphere ($N_2$). At room temperature, 81 μL of diisopropoxymethyl borane 97% (0.36 mmol, 1.3 eq.) is added. The reaction mixture is brought to 70° C. and stirred at this temperature for 30 minutes. The solvent is gently removed under reduced pressure within 15 minutes. 2 mL of toluene is added and the reaction mixture is cooled to −80° C. 240 μL (2 eq.) of a 2.7M solution of dimethylaminopropyl magnesium chloride in THF is slowly added (duration: 10 minutes). Stirring is continued for 10 minutes at −80° C. HPLC control indicated a conversion of >96%. The ratio of S-diol (4-[(S)-4-dimethylamino-1-(4-fluorophenyl)-1-hydroxy-butyl]-3-hydroxymethyl-benzonitrile) to R-diol (4-[(R)-4-dimethylamino-1-(4-fluorophenyl)-1-hydroxy-butyl]-3-hydroxymethyl-benzonitrile) is 15.9:84.1 (enantiomeric excess=68.2%).

Example 9

Quinidine as amino alcohol, −80 CC in toluene/methylene chloride, diisopropoxymethyl borane as linker 79 mg of 4-(4-fluorobenzoyl)-3-hydroxymethyl-benzonitrile (0.31 mmol, 1.0 eq.) and 100 mg of (−)-quinidine 98% (0.31 mmol, 1.0 eq.) are dissolved in a two-necked round bottomed flask in 2 mL of toluene under an inert atmosphere ($N_2$). At room temperature, 62 μL of diisopropoxymethyl borane 97% (0.32 mmol, 1.03 eq.) is added. The reaction mixture is brought to 70° C. and stirred at this temperature for 30 minutes. The solvent is gently removed under reduced pressure within 15 minutes. 2 mL of toluene and 2 mL of methylene chloride are added and the reaction mixture is cooled to −80° C. 230 μL (2 eq.) of a 2.7M solution of dimethylaminopropyl magnesium chloride in THF is slowly added (duration: 10 minutes). Stirring is continued for 10 minutes at −80° C. HPLC control indicated a conversion of >97%. The ratio of S-diol (4-[(S)-4-dimethylamino-1-(4-fluorophenyl)-1-hydroxy-butyl]-3-hydroxymethyl-benzonitrile) to R-diol (4-[(R)-4-dimethylamino-1-(4-fluorophenyl)-1-hydroxy-butyl]-3-hydroxymethyl-benzonitrile) is 86.3:13.7 (enantiomeric excess=72.7%).

Example 10

R-2-Dimethylamino-1-phenyl-ethanol as amino alcohol, −80° C. in toluene, diisopropoxymethyl borane as linker 131 mg of 4-(4-fluorobenzoyl)-3-hydroxymethyl-benzonitrile (0.51 mmol, 1.0 eq.) and 85 mg of R-2-dimethylamino-1-phenyl-ethanol 90% (0.46 mmol, 0.9 eq.) are dissolved in a two-necked round bottomed flask in 5 mL of toluene under an inert atmosphere ($N_2$). At room temperature, 108 μL of diisopropoxymethyl borane 97% (0.57 mmol, 1.1 eq.) is added. The reaction mixture is brought to 70° C. and stirred at this temperature for 30 minutes. The solvent is gently removed under reduced pressure within 15 minutes. 5 mL of toluene is added and the reaction mixture is cooled to −80° C. 312 μL (2 eq.) of a 3.3M solution of dimethylaminopropyl magnesium chloride in THF is slowly added (duration: 1 minute). Stirring is continued for 10 minutes at −80° C. HPLC control indicated a conversion of >97%. The ratio of S-diol (4-[(S)-4-dimethylamino-1-(4-fluorophenyl)-1-hydroxy-butyl]-3-hydroxymethyl-benzonitrile) to R-diol (4-[(R)-4-dimethylamino-1-(4-fluorophenyl)-1-hydroxy-butyl]-3-hydroxymethyl-benzonitrile) is 8.5:91.5 (enantiomeric excess=83.0%).

Example 11

S-1-Dimethylamino-2-propanol as amino alcohol, −80° C. in toluene, diisopropoxymethyl borane as linker 202 mg of 4-(4-fluorobenzoyl)-3-hydroxymethyl-benzonitrile (0.79 mmol, 1.0 eq.) and 105 μL of S-1-dimethylamino-2-propanol 98% (0.80 mmol, 1.02 eq.) are dissolved in a two-necked round bottomed flask in 3 mL of toluene under an inert atmosphere ($N_2$). At room temperature, 160 μL of diisopropoxymethyl borane 97% (0.86 mmol, 1.1 eq.) is added. The reaction mixture is brought to 45° C. and stirred at this temperature for 30 minutes. The solvent is gently removed under reduced pressure within 15 minutes. 3 mL of toluene is added and the reaction mixture is cooled to −80° C. 2.5 mL (3.1 eq.) of a 0.8M solution of dimethylaminopropyl magnesium chloride in THF is slowly added (duration: 1 minute). Stirring is continued for 10 minutes at −80° C. HPLC control indicated a conversion of >95%. The ratio of S-diol (4-[(S)-4-dimethylamino-1-(4-fluorophenyl)-1-hydroxy-butyl]-3-hydroxymethyl-benzonitrile) to R-diol (4-[(R)-4-dimethylamino-1-(4-fluorophenyl)-1-hydroxy-butyl]-3-hydroxymethyl-benzonitrile) is 75.5:24.5 (enantiomeric excess=51.0%).

Example 12

1S,2R—N-Methylephedrine as amino alcohol, −80° C., trimethylborate as linker 145 mg of 4-(4-fluorobenzoyl)-3-hydroxymethyl-benzonitrile (0.56 mmol, 1.0 eq.) and 100 mg of 1S,2R—N-methylephedrine 99% (0.56 mmol, 1.0 eq.) are dissolved in a two-necked round bottomed flask in 3 mL of toluene under an inert atmosphere ($N_2$). At room temperature, 160 μL of diisopropoxymethyl borane (0.59 mmol, 1.05 eq.) is added. The reaction mixture is brought to 70° C. and stirred at this temperature for 30 minutes. The solvent is gently removed under reduced pressure within 15 minutes. 3 mL of toluene is added and the reaction mixture is cooled to −80° C. 800 μL (2 eq.) of a 1.3M solution of dimethylaminopropyl magnesium chloride in THF is slowly added (duration: 2 minutes). Stirring is continued for 10 minutes at −80° C. HPLC control indicated a conversion of >90%. The ratio of S-diol (4-[(S)-4-dimethylamino-1-(4-fluorophenyl)-1-hydroxy-butyl]-3-hydroxymethyl-benzonitrile) to R-diol (4-[(R)-4-dimethylamino-1-(4-fluorophenyl)-1-hydroxy-butyl]-3-hydroxymethyl-benzonitrile) is 71.6:28.4 (enantiomeric excess=43.2%). About 10% of 4-[(4-fluorophenyl)-hydroxy-methyl]-3-hydroxymethyl-benzonitrile are formed as a byproduct.

Example 13

1S,2R—N-Methylephedrine as amino alcohol, −80° C., triisopropylborate as linker 142 mg of 4-(4-fluorobenzoyl)-3-hydroxymethyl-benzonitrile (0.56 mmol, 1.0 eq.) and 100 mg of 1S,2R—N- methylephedrine 99% (0.56 mmol, 1.0 eq.) are dissolved in a two-necked round bottomed flask in 2 mL of toluene under an inert atmosphere ($N_2$). At room temperature, 135 µL of diisopropoxymethyl borane (0.59 mmol, 1.05 eq.) is added. The reaction mixture is brought to 70° C. and stirred at this temperature for 30 minutes. The solvent is gently removed under reduced pressure within 15 minutes. 2 mL of toluene is added and the reaction mixture is cooled to −80° C. 412 µL (2 eq.) of a 2.7M solution of dimethylaminopropyl magnesium chloride in THF is slowly added (duration: 2 minutes). Stirring is continued for 10 minutes at −80° C. HPLC control indicated a conversion of >50%. The ratio of S-diol (4-[(S)-4-dimethylamino-1-(4-fluorophenyl)-1-hydroxy-butyl]-3-hydroxymethyl-benzonitrile) to R-diol (4-[(R)-4-dimethylamino-1-(4-fluorophenyl)-1-hydroxy-butyl]-3-hydroxymethyl-benzonitrile) is 72.2:27.8 (enantiomeric excess=44.4%).

Example 14

1S,2S-N-Methylephedrine as amino alcohol, −80° C. in toluene, 3,3-dimethylamino-1-propine as nucleophile, diisopropoxymethyl borane as linker 120 µL of 3,3-Dimethylamino-1-propine (1.13 mmol, 2.0 eq.) are dissolved in 1 mL of THF. At 0° C. 372 eq. of a 3M solution of dimethylaminopropyl magnesium chloride in THF are added. The resulting solution is stirred for 20 minutes.

In a second flask, 142 mg of 4-(4-fluorobenzoyl)-3-hydroxymethyl-benzonitrile (0.56 mmol, 1.0 eq.) and 100 mg of 1 S,2R—N-methylephedrine 99% (0.56 mmol, 1.0 eq.) are dissolved in a two-necked round bottomed flask in 2 mL of toluene under an inert atmosphere ($N_2$). At room temperature, 135 µL of diisopropoxymethyl borane (0.59 mmol, 1.05 eq.) is added. The reaction mixture is brought to 70° C. and stirred at this temperature for 30 minutes. The solvent is gently removed under reduced pressure within 15 minutes. 2 mL of toluene is added and the reaction mixture is cooled to −20° C. The solution containing the magnesium salt of 3,3-dimethylamino-1-propine is now added within 5 minutes. The reaction mixture is warmed to room temperature and stirred for 24 hours. HPLC control indicated a conversion of >70%. The ratio of 4-[(S)-4-dimethylamino-1-(4-fluorophenyl)-1-hydroxy-but-2-ynyl]-3-hydroxymethyl-benzonitrile to 4-[(R)-4-dimethylamino-1-(4-fluorophenyl)-1-hydroxy-but-2-ynyl]-3-hydroxymethyl-benzonitrile is 90:10 (enantiomeric excess=80%).

Example 15

Synthesis of 4-(4-fluorobenzoyl)-3-hydroxymethyl-benzonitrile (synthesis example)

1048 g of a 10% solution of 4-fluorophenylmagnesium bromide in tetrahydrofuran are added to a suspension of 60.0 g of 5-cyanophthalide in 390 ml of 1,2-dimethoxyethane at −10° C. within three hours. After stirring for 30 minutes at −10° C., the cold reaction mixture is poured into 1 L of aqueous $NH_4Cl$ (180 g in 1000 ml of water, 20° C.) in about 5 minutes. The layers are separated and the aqueous layer is extracted with 300 ml of tetrahydrofuran. The organic layers are combined and volatiles are removed under reduced pressure at 45° C. The residue is dissolved in a mixture of 1000 mL of $CH_2Cl_2$ and 200 ml of water containing 2.5 g of sodium carbonate (pH of 9). The layers are separated and the organic phase is dried with 40 g of sodium carbonate. The dry $CH_2Cl_2$ solution is treated with 6 g of charcoal, stirred for 10 minutes and the charcoal is removed by filtration. The filter cake is washed with 50 mL of $CH_2Cl_2$. Filtrate and washing liquid are combined and the solvent is removed under reduced pressure. 300 mL of diisopropylether are added to the residue. After stirring for 1 hour at 22° C. the crystal suspension is cooled to 0° C. and stirred for another two hours, then cooled to −10° C. and stirred for 14 hours. The product is isolated by filtration and washed with 40 mL of chilled diisopropylether, 80 mL of a 1:1 mixture of diisopropylether/cyclohexane and 80 mL of cyclohexane. After drying for 3 hours at 50° C. in vacuo 83.0 g (86.2% of theory, purity (HPLC): 99.8 area %) white, crystalline powder of the title compound are obtained (mp. 85° C.).

$^1$H-NMR (CDCl$_3$, 300 MHz): 3.01 (t, J=6.30, 0.8H, OH), 3.66 (s, 0.2H, OH), 4.66 (d, J=6.11 Hz, 1.6H, CH2-O), 5.33 (m, CH2-O, 0.4H, lactol-isomer), 7.03-7.93 (m, 7H, ArH)

Example 16

1S,2S-N-Methylpseudoephedrine as amino alcohol, −60° C., methylboronic acid as linker 250 mg of 4-(4-fluorobenzoyl)-3-hydroxymethyl-benzonitrile (0.98 mmol, 1.0 eq.) and 263 mg of 1S,2R—N-methylephedrine 99% (1.45 mmol, 1.48 eq.) are dissolved in a two-necked round bottomed flask in 15 mL of toluene under an inert atmosphere ($N_2$). At room temperature 67 mg of methylboronic acid (1.12 mmol, 1.14 eq.) is added. The reaction mixture is brought to 70° C. and stirred at this temperature for 30 minutes. The solvent is gently removed under reduced pressure within 15 minutes. 10 mL of toluene is added and again gently removed under reduced pressure. 5 mL of toluene is added and the reaction mixture is cooled to −60° C. 2.3 mL (2 eq.) of a 0.84M solution of dimethylaminopropyl magnesium chloride in THF is slowly added (duration: 2 minutes). Stirring is continued for 10 minutes at −60° C. HPLC control indicated a conversion of >98%. The ratio of S-diol (4-[(S)-4-dimethylamino-1-(4-fluorophenyl)-1-hydroxy-butyl]-3-hydroxymethyl-benzonitrile) to R-diol (4-[(R)-4-dimethylamino-1-(4-fluorophenyl)-1-hydroxy-butyl]-3-hydroxymethyl-benzonitrile) is 96.3:3.7 (enantiomeric excess=92.6%).

Example 17

Synthesis and isolation of (S)-4-(4-dimethylamino)-1-(4-fluorophenyl)-1-hydroxybutyl-3-hydroxymethyl-benzonitrile, hemi (+)-di-p-toluoyl-tartaric acid salt; (S)-2-N,N-dimethylaminophenylethanol as auxiliary 10.0 g of 4-(4-fluorobenzoyl)-3-hydroxymethyl-benzonitrile (MW: 255.25, assay: 96.7%; 37.9 mmol) are dissolved in 140 mL of toluene. 7.77 g of (S)-2-N,N-dimethylaminophenylethanol (MW: 165.24, 47.0 mmol, 1.24 eq.) and 2.51 g of methylboronic acid (MW: 59.86, assay: 98%, 41.1 mmol, 1.08 eq.) are added. The solution becomes slightly turbid and drops of water are rapidly formed. The mixture is heated to 50° C. At reduced pressure (~60-70 mbar) ~100 mL of toluene/water is carefully removed. 100 mL of toluene is added and ~100 mL of toluene/water is removed. 120 mL of toluene are added and about ~20 mL of toluene/water is removed to get a solution of mixed boronate (~80 mmol) in about 250 mL of solvent. The water content is below 0.1% as determined by a Karl Fischer titration. The reaction mixture is cooled to −65° C. Within about 10-20 minutes 38.0 mL of a ~2M solution of dimethylaminopropyl magnesiumchloride in THF (~2 eq.) are added. Thereby, the temperature does not exceed −50° C. The solution is stirred for another 30 minutes. Reaction control is performed with HPLC (ee=90%). After complete conversion (area % 4-(4-fluorobenzoyl)-3-hydroxymethyl-benzonitrile<2%) the reaction mixture is processed further.

20 mL of water and 35 mL of 2M aqueous $H_2SO_4$ (70 mmol) are added to get a pH of ~1.5 in the aqueous layer. After phase separation, the organic layer is washed once with 20 mL water, adjusted to pH 1 with 2M aqueous $H_2SO_4$.150 mL of $CH_2Cl_2$ is added to the combined aqueous layers. 7M aqueous $NH_3$ is now added (29 mL) until a pH of ~9.0 is reached. After phase separation the aqueous layer is washed twice with 25 mL of MED (at pH 9.0). The combined $CH_2Cl_2$ layers are washed with 15 mL of water. 70 mL of $H_2O$ are added. 10.7 mL of 2M aqueous $H_2SO_4$ are added to adjust the pH to 6.4. After stirring for 10 minutes the layers are separated (pH 6.4). 35 mL of water is added to the $CH_2Cl_2$ layer. Addition of 1.5 mL of 2M aqueous $H_2SO_4$ gives a pH of 6.4. After stirring for 10 minutes the layers are separated. 80 mL of $CH_2Cl_2$ are added to the combined aqueous layers. Addition of 2 mL of 7M aqueous $NH_3$ gives a pH of 6.4 (after equilibration). The layers are separated. The combined organic layers are washed with 20 mL of water. The layers are separated. The combined $CH_2Cl_2$ layer contains the enantiomerically enriched diol. The combined aqueous layer contains ~90% of the chiral auxiliary. 200 mL of $CH_2Cl_2$ is removed. 60 mL of 2-propanol is added. 30 mL of 2-propanol/$CH_2Cl_2$ is removed under reduced pressure. 30 mL of 2-propanol is added to obtain ~13 g of CIT-DIOL in 60 mL of ISO. To this solution 6.59 g of (+)-ditoluoyl tartaric acid (MW: 386.36; assay: 99%; 17.1 mmol, 0.45 eq.), dissolved in 42 mL of 2-propanol and 8 mL of $CH_2Cl_2$, is added. The product starts to crystallize after 5 minutes (or immediately after seeding). The mixture is stirred for 90 minutes at 35° C., for 10 minutes at 60° C. and than slowly cooled down to room temperature (within ~5 hours) and crystallized without stirring for 10 hours. The product is isolated by filtration to give 17.2 g of S-CIT-DIOL.½(+)-DTTA.½ISO.½H₂O (yield: 81.0%; ee: 99.0%, assay: 61.0%) after drying for 10 hours at 40° C. and 20 mbar.

Example 18

Synthesis and isolation of (S)-4-(4-dimethylamino)-1-(4-fluorophenyl)-1-hydroxybutyl-3-hydroxymethyl-benzonitrile, hemi (+)-di-p-toluoyl-tartaric acid salt; 1S,2S-N-methylpseudoephedrine as auxiliary 20.68 g of 4-(4-fluorobenzoyl)-3-hydroxymethyl-benzonitrile (255.25, assay: 96.7%; 81.0 mmol) are dissolved in 280 mL of toluene. 16.05 g of 1S, 2S-N-methylpseudoephedrine (MW: 179.26, assay: 99.1%, 89.5 mmol, 1.1 eq.) and 5.02 g of methylboronic acid (MW: 59.86, assay: 98%, 82.2 mmol, 1.02 eq.) are added. The solution becomes slightly turbid and drops of water are rapidly formed. The mixture is heated to 50° C. At reduced pressure (~60-70 mbar) ~200-220 mL of toluene/water is carefully removed. 200 mL of toluene is added and 190-210 mL of toluene/water is removed. 200 mL of toluene is added and about 30 mL of toluene is removed to get a solution of mixed boronate (~80 mmol) in about 250 mL of solvent (water content<0.1%). The reaction mixture is cooled to −40° C. Within about 10-20 minutes 78.5 mL of a ~2M solution of dimethylaminopropyl magnesium chloride in THF (~2 eq.) is added. Thereby, the temperature does not exceed −35° C. The solution is stirred for another 30 minutes. Reaction control is performed by HPLC (ee=~92%). After complete conversion the reaction mixture is processed further. 85 mL of 2M aqueous $H_2SO_4$ (170 mmol) is added within 5 minutes. The final pH of the aqueous layer is ~2. The organic layer is washed twice with 5 mL of 2M aqueous $H_2SO_4$.300 mL of methyl tert-butyl ether is added to the combined aqueous layers. 7M aqueous $NH_3$ is now added until a pH of 9.2 is reached. After phase separation the aqueous layer is washed twice with 100 mL of methyl tert-butyl ether (at pH 9.2). The combined methyl tert-butyl ether layers is washed twice with 20 mL of 7M aqueous $NH_3$. About 400 mL of the methyl tert-butyl ether is removed under reduced pressure. Methyl tert-butyl ether is added to a total volume of about 250 mL. 24.8 g of pivalic acid (MW: 102.14; 242 mmol, 3.0 eq.) is dissolved in 80 mL of methyl tert-butyl ether. This solution is added to the diol solution in methyl tert-butyl ether. 1S,2S-N-methylpseudoephedrine pivalic acid salt rapidly crystallizes. The mixture is carefully stirred for 30 minutes at room temperature and 30 minutes at 0° C. NMPE.PIVOH is removed by filtration. The filter cake is washed with 75 mL of methyl tert-butyl ether. After drying (20 mbar, 40° C., 1 hour) 19.8 g of 1S,2S-N-methylpseudoephedrine pivalic acid salt are obtained (yield: 79%; assay: 98.8%).

The combined methyl tert-butyl ether layers is washed with 60 mL of 7M aqueous $NH_3$ and 20 mL of water. The layers are separated. About ⅔ of methyl tert-butyl ether is removed under reduced pressure to give a concentrated solution of enantiomerically enriched diol in methyl tert-butyl ether (60 mL). 100 mL of 2-propanol are added and the methyl tert-butyl ether/2-propanol is removed to a final volume of about 60 mL. 90 mL of 2-propanol is added to obtain ~26 g of diol in about 120 mL of 2-propanol. 15.5 g of (+)-ditoluoyl tartaric acid (MW: 386.36; assay: 99%; 40.1 mmol, 0.49 eq.) dissolved in 80 mL of 2-propanol is added to this solution. The product starts to crystallize after 5 minutes (or immediately after seeding). The mixture is stirred for 1 hour at 30° C., for 10 minutes at 60° C. and than slowly cooled down to room temperature (within ~5 hours) and crystallized without stirring for 10 hours. The product is isolated by filtration to give 33.86 g of (S)-4-(4-dimethylamino)-1-(4-fluorophenyl)-1-hydroxybutyl-3-hydroxymethyl-benzonitrile, hemi (+)-di-p-toluoyl-tartaric acid salt (yield: 76.7%; ee: 99.3%, assay: 60.7%) after drying for 6 hours at 40° C. and 20 mbar.

Example 19

Synthesis and Isolation of Escitalopram Oxalate (S)-4-(4-Dimethylamino)-1-(4'-fluorophenyl)-1-hydroxybutyl-3-hydroxymethylbenzonitrile, hemi (+)-di-p-toluoyl-tartaric acid salt (16.64 g; 29.7 mmol) is suspended in a mixture of 180 ml water and 180 ml dichloromethane. After pH-correction with aqueous ammonia to pH 9 the phases are separated. Triethylamine (5.7 ml; 41 mmol) is added to the cooled and dried organic phase (100 ml) followed by p-toluolsulfonyl chloride (6.1 g; 32 mmol) and the resulting solution is stirred for one hour at a temperature below 5° C. Subsequently the reaction mixture is washed with water at pH 6 and pH 12, followed by a concentrating step under reduced pressure and dilution with acetone. Oxalic acid (2.52 g; 28 mmol) is added to the final solution and escitalopram oxalate crystallizes. The crystals are collected by filtration and washed with cold acetone. The wet cake is dried in vacuum to give 11.4 g of escitalopram oxalate. (purity HPLC: 99.7%; ee=98.8%).

$^1$H-NMR (DMSO-d$_6$, 300 MHz): 1.39-1.60 (m, 2H, $CH_2$), 2.21-2.27 (t, 2H, $CH_2$) 2.50 (s, 3H, $CH_3$), 2.51 (s, 3H, $CH_3$), 2.94-2.99 (t, 2H, $CH_2$), 5.13-5.26 (q, 2H, $CH_2$), 7.11-7.19 (m, 2H, aryl), 7.54-7.61 (m, 2H, aryl), 7.61-7.68 (m, 3H, aryl).

Example 20

Asymmetric synthesis of enantiomerically enriched 5-(dimethylamino)-2-phenylpentane-1,2-diol

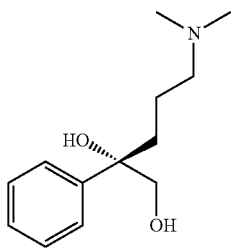

500 mg of 2-hydroxyacetophenone (3.60 mmol, 1.00 eq), 798 mg of (1S,2S)-2-dimethylamino-1-phenylpropane-1-ol (1S, 2S-NMPE, 4.45 mmol, 1.20 eq) and 231 mg of methylboronic acid (3.89 mmol, 1.05 eq) were dissolved in 10 mL of toluene. At a bath temperature of 25° C. and 15 mbar 8 mL toluene/water was removed under reduced pressure. 8 mL of toluene and 800 mg of molecular sieves type 5 Å were added. The suspension was stirred for 15 hours at −20° C.

The molecular sieves were removed by filtration and 5.8 mL of a 1.5M solution of dimethylaminopropylmagnesium chloride in THF (8.7 mmol, 2.42 eq) were added within 130 minutes at a bath temperature of −70° C. The reaction was stopped by addition of 17 mL of aqueous 1M KHSO$_4$. The layers were separated. The pH of the aqueous layer was adjusted to 10 by addition of 5M aqueous NaOH and extracted twice with 5 mL of methylene chloride. The combined organic layer was dried with Na$_2$SO$_4$, filtrated, and the solvent was removed under reduced pressure.

The crude product was dissolved in 10 mL of Et$_2$O. 1.6 g Celite® were added and the solvent was removed under reduced pressure. The crude product on Celite® was further purified by column chromatography on silica gel. (20 g of SiO$_2$, eluent: ethylacetate/triethylamine 200+5).

Yield: 760 mg, 95%; crystalline white solid; melting point: 50° C.

ee=80% (determined after derivatization as described in: Kelly, A. M.; Perez-Fuertes, Y.; Arimori, S.; Bull, S. D. *Org. Lett.* 2006, 8, 1971)

$^1$H-NMR (CDCl$_3$): δ 1.23-1.40 (m. 2H), 1.90-2.15 (m, 2H), 2.08 (s, 6H), 2.30 (m, 2H), 3.53 (d, 1H, J=10.8 Hz), 3.55 (d, 1H, J=10.8 Hz), 7.21 (m, 1H), 7.31 (m, 2H), 7.41 (m, 2H).

$^{13}$C-NMR (CDCl$_3$): 21.8, 37.6, 44.9 (2C), 60.0, 72.3, 75.6, 126.0 (2C), 126.5, 128.2 (2C), 145.3.

Example 21

Asymmetric synthesis of enantiomerically enriched 3-(4-fluorophenyl)butane-1,3-diol

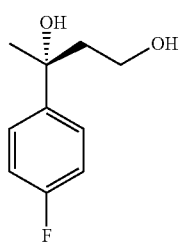

500 mg of 4-hydroxy-2-butanone (5.39 mmol, 1.00 eq), 1990 mg of (R)-(quinolin-4-yl)((2R,4S,5R)-5-vinylquinuclidin-2-yl)methanol (cinchonidine, 6.47 mmol, 1.20 eq), 340 mg of methylboronic acid (5.66 mmol, 1.05 eq) were dissolved in 15 mL of toluene. At 25° C. and under reduced pressure (10 mbar) ~8 mL of toluene/water was azeotropically removed. ~8 mL of toluene was added and again removed under reduced pressure. 5 mL of toluene and 300 mg of molecular sieves type 5 Å were added. The reaction mixture was stirred for 10-15 hours at −20° C.

The molecular sieves were removed by filtration. At a temperature of −60° C. 13 mL of 0.83M 4-fluorophenylmagnesium bromide in THF (10.8 mmol, 2.00 eq) were added. The conversion was determined by TLC (eluent: ethyl acetate/cyclohexane 1+1). The reaction was quenched after 45 minutes by addition of 10 mL of 2.5M aqueous NaOH. The layers were separated and the organic layer was washed twice with 10 mL of 1M aqueous KHSO$_4$, and once with 10 mL of sat. aqueous NaHCO$_3$.

The combined organic layer was dried with Na$_2$SO$_4$, filtrated, and the solvent was removed under reduced pressure.

The crude product was dissolved in 10 mL of Et$_2$O. 2 g of Celite® was added and the solvent was removed under reduced pressure. The crude product on Celite® was further purified by column chromatography on silica gel. (14 g of SiO$_2$, eluent: ethylacetate/cyclohexane 1+10).

Yield: 665 mg, 83%; crystalline white solid; melting point: 73° C.

ee=55% (HPLC)

$^1$H-NMR (DMSO-d6): δ 1.42 (s, 3H), 1.90 (t, 2H, J=7.3 Hz), 2.50 (s, OH, 1H), 3.27 (m, 1H), 3.42 (m, 1H), 7.09 (m, 2H), 7.44 (m, 2H).

$^{13}$C-NMR (DMSO-d6): δ 30.8, 46.2, 57.8, 72.7, 114.3, 114.6, 126.9, 127.0, 142.0, 161.7 (d, J$_{CF}$=242.6 Hz).

Example 22

Asymmetric synthesis of enantiomerically enriched 4-butyl-2-methyl-4-phenyl-1,3,2-dioxaborolane

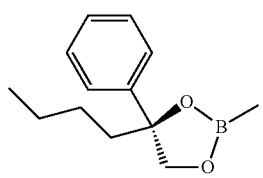

500 mg of 2-hydroxyacetophenone (3.60 mmol, 1.00 eq), 798 mg of (1S,2S)-2-dimethylamino-1-phenylpropane-1-ol (1S,2S-NMPE, 4.45 mmol, 1.20 eq) and 231 mg of methylboronic acid (3.89 mmol, 1.05 eq) were dissolved in 10 mL of toluene. At 25° C. and under reduced pressure (10-15 mbar) ~8 mL of toluene/water was azeotropically removed. ~8 mL of toluene was added and again removed under reduced pressure. 5 mL of toluene and 400 mg of molecular sieves type 5 Å were added. The reaction mixture was stirred for 5 hours at 20° C.

At a temperature of −70° C., 3.6 mL of a 2M solution of butylmagnesium chloride in THF (7.20 mmol, 2.00 eq) was added. The conversion was determined by TLC (eluent: ethyl acetate/cyclohexane 1+10). The reaction was quenched after 45 minutes by addition of 15 mL of 1M aqueous KHSO$_4$. The layers were separated and the organic layer was washed with 10 mL of 1M aqueous KHSO$_4$, then twice with 10 mL of sat. aqueous NaHCO$_3$.

The combined organic layer was dried with $Na_2SO_4$, filtrated, and the solvent was removed under reduced pressure.

The crude product was dissolved in 10 mL of $Et_2O$. 1.1 g of Celite® was added and the solvent was removed under reduced pressure. The crude product on Celite® was further purified by column chromatography on silica gel. (20 g of $SiO_2$, eluent: ethylacetate/cyclohexane 1+10).

Yield: 110 mg; oil.

$^1$H-NMR ($CDCl_3$): δ 0.44 (s, 3H), 0.89 (t, 3H, J=7.0 Hz), 1.15 (m, 1H), 1.36 (m, 3H), 1.91 (m, 2H), 4.24 (d, 1H, J=8.8 Hz), 4.33 (d, 1H, J=8.8 Hz), 7.34 (m, 5H).

$^{13}$C-NMR ($CDCl_3$): δ 14.1, 22.9, 25.8, 42.8, 77.2, 85.4, 124.6, 125.6, 127.1, 127.4, 128.4, 145.7.

For the determination of the ee the boronate was hydrolysed with aqueous $H_2O_2$. The ee was determined by HPLC (ee=40%).

Example 23

Asymmetric synthesis of enantiomerically enriched 4-(1-(4-fluorophenyl)-1-hydroxy-3-methylbutyl)-3-(hydroxymethyl)benzonitrile

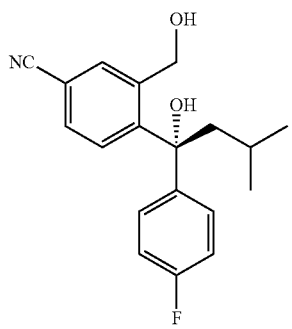

500 mg of 4-(4-fluorobenzoyl)-3-(hydroxymethyl)benzonitrile (1.96 mmol, 1.00 eq), 425 mg of (1S,2S)-2-dimethylamino-1-phenylpropane-1-ol (1S,2S-NMPE, 2.37 mmol, 1.20 eq) and 126 mg of methylboronic acid (2.10 mmol, 1.05 eq) were dissolved in 10 mL of toluene. At 35° C. and under reduced pressure (10-15 mbar) ~7 mL of toluene/water was azeotropically removed. ~7 mL of toluene was added and again removed under reduced pressure. 5 mL of toluene and 200 mg of molecular sieves type 5 Å were added. The reaction mixture was stirred for 3 hours at 25° C.

At a temperature of −70° C., 2.5 mL of a 2M solution of isobutylmagnesium chloride in THF (5.0 mmol, 2.6 eq) were added. The conversion was determined by TLC (eluent: ethyl acetate/cyclohexane 1+1). The reaction was quenched after 120 minutes by addition of 15 mL of 1M aqueous $KHSO_4$. The layers were separated and the organic layer was washed with 10 mL of 1M aqueous $KHSO_4$, then twice with 10 mL of sat. aqueous $NaHCO_3$.

The combined organic layer was dried with $Na_2SO_4$, filtrated, and the solvent was removed under reduced pressure.

The crude product was dissolved in 10 mL of $Et_2O$. 1.1 g of Celite® was added and the solvent was removed under reduced pressure. The crude product on Celite® was further purified by column chromatography on silica gel. (20 g of $SiO_2$, eluent: ethylacetate/cyclohexane 1+10).

Yield: 180 mg of 4-(1-(4-fluorophenyl)-1-hydroxy-3-methylbutyl)-3-(hydroxymethyl)benzonitrile; ee=60%; white crystalline solid; melting point: 82° C.

$^1$H-NMR ($CDCl_3$): δ 0.73 (d, 3H, J=6.7 Hz), 0.96 (d, 3H, J=6.7 Hz), 1.51 (m, 1H), 2.17 (m, 2H), 3.60 (s, OH), 4.21 (d, 1H, J=12.9 Hz), 4.29 (d, 1H, J=12.9 Hz), 6.99 (m, 2H), 7.26 (m, 2H), 7.58-7.74 (m, 3H).

$^{13}$C-NMR ($CDCl_3$): δ 23.8, 24.9, 27.0, 51.5, 63.6, 79.2, 111.6, 115.0, 115.3, 118.5, 127.5, 127.5, 127.6, 131.4, 135.0, 140.7, 141.4, 151.0, 161.7 (d, $J_{CF}$=247.2 Hz).

295 mg of 4-((4-fluorophenyl)(hydroxy)methyl)-3-(hydroxymethyl)-benzonitrile, colorless oil; ee=60%, (determined after derivatization as described in: Kelly, A. M.; Pérez-Fuertes, Y.; Arimori, S.; Bull, S. D. *Org. Lett.* 2006, 8, 1971)

$^1$H-NMR ($CDCl_3$): δ 0.73 (d, 3H, J=6.7 Hz), 0.96 (d, 3H, J=6.7 Hz), 1.51 (m, 1H), 2.17 (m, 2H), 3.60 (s, OH), 4.21 (d, 1H, J=12.9 Hz), 4.29 (d, 1H, J=12.9 Hz), 6.99 (m, 2H), 7.26 (m, 2H), 7.58-7.74 (m, 3H).

$^{13}$C-NMR ($CDCl_3$): δ 23.78, 24.87, 27.00, 51.53, 63.57, 79.18, 111.58, 115.04, 115.33, 118.50, 127.48, 127.54, 127.58, 131.42, 134.96, 140.66, 141.37, 150.95, 161.74 (d, $J_{CF}$=247.2 Hz).

Example 24

Asymmetric synthesis of enantiomerically enriched 4-(1-(4-fluorophenyl)-1-hydroxypentyl)-3-(hydroxymethyl)-benzonitrile

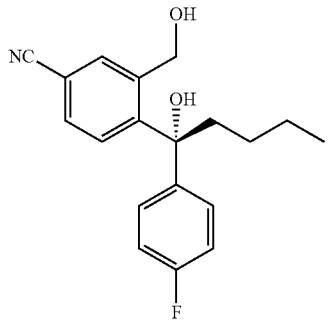

1000 mg of 4-(4-fluorobenzoyl)-3-(hydroxymethyl)benzonitrile (3.92 mmol, 1.00 eq), 840 mg of (1S,2S)-2-dimethylamino-1-phenylpropane-1-ol (1S,2S-NMPE, 4.68 mmol, 1.20 eq) and 250 mg of methylboronic acid (4.20 mmol, 1.05 eq) were dissolved in 30 mL of toluene. At 65° C. and under reduced pressure (85-110 mbar) ~20 mL of toluene/water were azeotropically removed. 20 mL of toluene and 500 mg of molecular sieves type 5 Å were added. The reaction mixture was stirred for 60 minutes at 25° C.

At a temperature of −50° C., 3.9 mL of a 2M solution of butylmagnesium chloride in THF were added. The conversion was determined by TLC (eluent: ethyl acetate/cyclohexane 1+1). After 50 minutes the mixture was filtrated and then quenched by addition of 10 mL of 1M aqueous $KHSO_4$. The layers were separated and the organic layer was washed twice with 10 mL of sat. aqueous $NaHCO_3$.

The combined organic layer was dried with $Na_2SO_4$, filtrated, and the solvent was removed under reduced pressure.

The crude product was dissolved in 15 mL of methylene chloride. 4 g of Celite® were added and the solvent was removed under reduced pressure. The crude product on Celite® was further purified by column chromatography on silica gel. (40 g of $SiO_2$, eluent: ethylacetate/cyclohexane 1+5).

Yield: 675 mg (57%); ee=91%; slightly yellow oil.

$^1$H-NMR (CDCl$_3$): δ 0.90 (t, 3H, J=7.0 Hz), 1.11 (m, 1H), 1.32 (m, 3H), 2.2 (m, 2H), 4.14 (d, 1H, J=12.9 Hz), 4.26 (d, 1H, J=12.9 Hz), 6.97 (t, 2H, J=8.6 Hz), 7.20 (m, 2H), 7.52 (s, 1H), 7.64 (m, 2H).

$^{13}$C-NMR (CDCl$_3$): δ 14.0, 23.0, 25.5, 42.9, 63.4, 78.6, 111.4, 114.8, 115.1, 118.5, 127.3, 127.4, 127.6, 131.4, 134.8, 140.8, 141.3, 150.5, 161.7 (d, J$_{CF}$=247.2).

The invention claimed is:

1. A process for the asymmetric alkylation of a carbonyl group in a compound (compound K) containing a carbonyl group and an anchor group that reacts with a boric or boronic acid derivative, comprising the steps of:
   a) admixing the compound K with a boric or boronic acid derivative;
   b) adding a chiral auxiliary (compound A); and
   c) adding an organometallic compound, wherein the steps a), b) and c) are conducted in any order or simultaneously wherein the boric or boronic acid derivative is a compound of formula VI,

wherein R$_1$ is hydrogen, C$_{1-10}$-alkyl, C$_{2-10}$-alkenyl, C$_{2-10}$-alkynyl, C$_{6-10}$-aryl, C$_{7-16}$ alkaryl, a 4-10 membered heterocyclic residue, C$_{1-10}$-alkoxy, C$_{1-10}$-alkylamino, C$_{1-10}$-alkylthio, hydroxy, or cyano;
and wherein R$_2$ is halogen, hydroxy, C$_{1-10}$-alkoxy, C$_{6-10}$-aryloxy, C$_{1-10}$-dialkylamino, or a 4-10 membered heterocyclic residue connected by a S, N, or O atom to the boron atom;
and wherein R$_3$ is halogen, amino, hydroxy, C$_{1-10}$-alkoxy, C$_{6-10}$-aryloxy, C$_{1-10}$-dialkylamino, or a 4-10 membered heterocyclic residue connected by a S, N, or O atom to the boron atom;
or wherein R$_2$ and R$_3$ are connected to each other to form a 5-10 membered cyclic structure including the boron atom to which R$_2$ and R$_3$ are connected, wherein the cyclic structure may contain one or two additional boron, and/or oxygen, and for nitrogen atoms.

2. The process of claim 1, wherein the steps a), b) and c) are conducted in a one-pot format.

3. The process of claim 1, wherein the order of steps a and b is reversed or wherein the boric or boronic acid derivative and the chiral auxiliary (compound A) are added simultaneously to the compound K.

4. The process of claim 1, wherein the steps a) and b) are conducted first and a distillation step is conducted before step c.

5. The process of claim 1, wherein R$_1$ is C$_{1-10}$-alkyl or C$_{1-10}$-alkoxy.

6. The process of claim 1, wherein R$_2$ and R$_3$ are hydroxy or C$_{1-10}$-alkoxy.

7. The process of claim 1, wherein the boric or boronic acid derivative is selected from the group consisting of phenylboronic acid, trimethylborate, triisopropylborate, diisopropylbutylboronate, diisopropylmethylboronate, methylboronic acid or trimethylboroxine.

8. The process of claim 1, wherein the anchor group is selected from the group consisting of hydroxyl, monosubstituted or unsubstituted amine, carboxyl and sulfhydryl.

9. The process of claim 8, wherein the anchor group is a hydroxyl group.

10. The process of claim 1, wherein the chiral auxiliary is a chiral alcohol of formula (VII)

wherein C* is a chiral carbon, n is an integer from 0 to 3 and X is a heteroatom having a free electron pair.

11. The process of claim 10, wherein n is 1 and X is nitrogen.

12. The process of claim 10, wherein the chiral alcohol is a chiral amino alcohol.

13. The process of claim 12, wherein the chiral amino alcohol is selected from the group consisting of N-methylephedrine, N-methylpseudoephedrine, 2-dimethylamino-1-phenylethanol, quinine, quinidine, cinchonidine, and cinchonine.

14. The process of claim 1, wherein the organometallic compound is selected from the group consisting of an organomagnesium, organozinc, organocadmium, organocerium, organolithium, organotitanium, organomanganese, organoiron, organoaluminum and organotin compound.

15. The process of claim 14, wherein the organomagnesium compound is selected from the group consisting of alkylmagnesium, alkenylmagnesium, and alkinylmagnesium.

16. The process of claim 1, wherein compound K has formula (III)

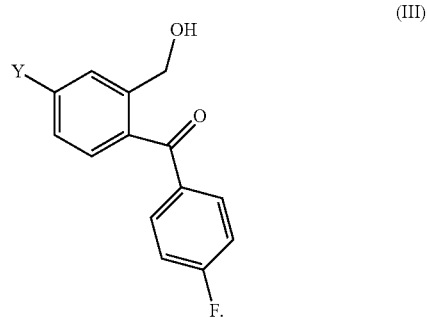

wherein Y is cyano or a group which is convertible to a cyano group.

17. The process of claim 16, wherein the organometallic compound is an organometallic compound of formula VIII

wherein the dotted line is a single, double, or triple bond.

18. The process of claim 17, wherein M is Mg and wherein Z is —CH$_2$—N(CH$_3$)$_2$ or a group that may be converted to —CH$_2$—N(CH$_3$)$_2$, wherein a diol of formula (II) is obtained in enantiomerically enriched or enantiomerically pure form

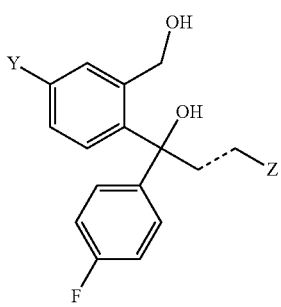

(II)

wherein Y is cyano or a group which is convertible to a cyano group.

19. The process of claim 18, further comprising the step of ring closure of the diol of formula (II) to form a compound of formula (IX)

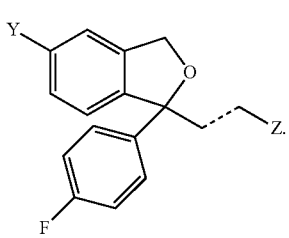

(IX)

20. The process of claim 19, wherein the compound of formula (IX) is escitalopram.

21. A compound of formula V

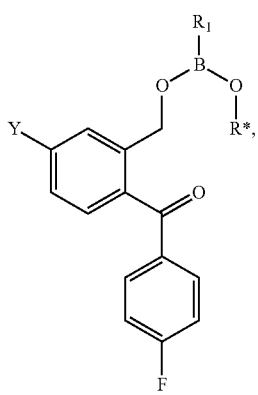

(V)

wherein $R_1$ is $C_{1-10}$-alkyl or $C_{1-10}$-alkoxy, wherein Y is cyano or a group which is convertible to a cyano group; and wherein O—R* is the residue of a chiral alcohol.

22. The compound of claim 21, wherein the group which is convertible to a cyano group is chloro, bromo, iodo, or $CF_3$—$(CF_2)_n$—$SO_2$—O—, wherein n is 0-8, $CH_2OH$ or protected $CH_2OH$, $CH_2NH_2$ or a protected $CH_2NH_2$, —$CH_2Cl$, —$CH_2Br$, —$CH_3$, —$NHR_2$, —$OR_2$, wherein $R_2$ is hydrogen or $C_{1-6}$ alkylcarbonyl; $CONR_3R_4$ wherein $R_3$ and $R_4$ are selected from hydrogen, optionally substituted $C_{1-6}$ alkyl, aryl-$C_{1-6}$ alkyl or aryl, or $R_3$ and $R_4$ are linked together to form a 5- or 6-membered ring optionally comprising a S, O, or additional N atom; or $CHOR_5OR_6$ wherein $R_5$ and $R_6$ are independently selected from alkyl, aryl, heteroaryl, or $R_5$ and $R_6$ are linked together to form a 5- or 6-membered ring; or other protected —CHO groups, and Y also includes optionally substituted oxazole, 4,5-dihydrooxazole, thiazole, or 4,5-dihydrothiazole groups.

23. A process for producing a desired enantiomer comprising:
performing asymmetric alkylation of a carbonyl group in a compound (compound K) containing a carbonyl group and an anchor group by mixing the compound K with a boric or boronic acid derivative, a chiral auxiliary (compound A), and an organometallic compound, under conditions where the boric or boronic acid derivative forms a link between the anchor group and the chiral auxiliary to form a boronate or borate, and the organometallic compound reacts with the carbonyl group to add a functional group from the organometallic compound to the compound K; and
removing the boronate or borate from the compound K to form the desired enantiomer, wherein the desired enantiomer is produced in an enantiomeric excess of greater than 50% without separation of any produced undesired enantiomer from the desired enantiomer wherein the boric or boronic acid derivative is a compound of formula VI,

(VI)

wherein $R_1$ is hydrogen, $C_{1-10}$-alkyl, $C_{2-10}$-alkenyl, $C_{2-10}$-alkynyl, $C_{6-10}$-aryl, $C_{7-16}$ alkaryl, a 4-10 membered heterocyclic residue, $C_{1-10}$-alkoxy, $C_{1-10}$-alkylamino, $C_{1-10}$-alkylthio, hydroxy, or cyano;
and wherein $R_2$ is halogen, hydroxy, $C_{1-10}$-alkoxy, $C_{6-10}$-aryloxy, $C_{1-10}$-dialkylamino, or a 4-10 membered heterocyclic residue connected by a S, N, or O atom to the boron atom;
and wherein $R_3$ is halogen, amino, hydroxy, $C_{1-10}$-alkoxy, $C_{6-10}$-aryloxy, $C_{1-10}$-dialkylamino, or a 4-10 membered heterocyclic residue connected by a S, N, or O atom to the boron atom;
or wherein $R_2$ and $R_3$ are connected to each other to form a 5-10 membered cyclic structure including the boron atom to which $R_2$ and $R_3$ are connected, wherein the cyclic structure may contain one or two additional boron, and/or oxygen, and/or nitrogen atoms.

24. The process according to claim 23, wherein the desired enantiomer is produced without separation of the undesired enantiomer in an amount of desired enantiomer to undesired enantiomer of at least 10 to 1.

25. The process according to claim 23, wherein the desired enantiomer is produced without separation of the undesired enantiomer in an amount of desired enantiomer to undesired enantiomer of at least 15 to 1.

26. The process according to claim 23, wherein the compound K, the boric or boronic acid, and the chiral auxiliary are combined first under conditions where the boric or boronic acid derivative forms the link between the anchor group and the chiral auxiliary and produces side products, and at least a portion of the side products is removed prior to the addition of the organometallic compound.

27. The process according to claim 23, wherein the desired enantiomer is produced in an enantiomeric excess of greater than 90% without separation of the undesired enantiomer from the desired enantiomer.

28. The process according to claim 23, wherein the desired enantiomer is a diol of formula (II)

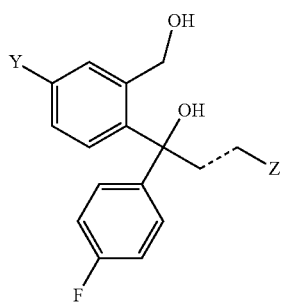

(II)

where Z is —CH$_2$—N(CH$_3$)$_2$ or a group that may be converted to —CH$_2$—N(CH$_3$)$_2$ and Y is cyano or a group which is convertible to a cyano group, and the process further comprises performing ring closure of the desired enantiomer to produce escitalopram.

29. The process according to claim 23, wherein the compound K is selected from the group consisting of alpha-, beta-, gamma- and delta-hydroxy-ketones or aldehydes, alpha-, beta-, gamma- and delta-amino-ketones or aldehydes, and alpha-, beta-, gamma- and delta-sulfhydryl-ketones or aldehydes.

* * * * *